(12) United States Patent
Reunamaki et al.

(10) Patent No.: US 10,748,402 B2
(45) Date of Patent: Aug. 18, 2020

(54) METHOD AND APPARATUS FOR MATCHING VITAL SIGN INFORMATION TO A CONCURRENTLY RECORDED DATA SET

(71) Applicant: Nokia Technologies Oy, Espoo (FI)

(72) Inventors: Jukka Reunamaki, Tampere (FI); Arto Palin, Viiala (FI)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 16/302,215

(22) PCT Filed: May 20, 2016

(86) PCT No.: PCT/FI2016/050347
§ 371 (c)(1),
(2) Date: Nov. 16, 2018

(87) PCT Pub. No.: WO2017/198894
PCT Pub. Date: Nov. 23, 2017

(65) Prior Publication Data
US 2019/0279479 A1   Sep. 12, 2019

(51) Int. Cl.
| | | |
|---|---|---|
| G08B 1/08 | (2006.01) | |
| G08B 21/02 | (2006.01) | |
| G08B 25/08 | (2006.01) | |
| G08B 21/04 | (2006.01) | |
| A61B 5/11 | (2006.01) | |

(Continued)

(52) U.S. Cl.
CPC ............ *G08B 21/02* (2013.01); *A61B 5/002* (2013.01); *A61B 5/0205* (2013.01); *A61B 5/0507* (2013.01); *A61B 5/1102* (2013.01); *A61B 5/113* (2013.01); *A61B 5/747* (2013.01); *G01S 7/41* (2013.01); *G01S 13/88* (2013.01); *G08B 21/04* (2013.01); *G08B 21/0446* (2013.01); *G08B 25/08* (2013.01); *G16H 10/60* (2018.01);

(Continued)

(58) Field of Classification Search
None
See application file for complete search history.

(56) References Cited

U.S. PATENT DOCUMENTS 5,798,798 A * 8/1998 Rector ................ G06F 19/3418
348/476
7,916,066 B1   3/2011 Osterweil ....................... 342/28

(Continued)

FOREIGN PATENT DOCUMENTS

WO    WO 02/082999 A1    10/2002

*Primary Examiner* — Adolf Dsouza
(74) *Attorney, Agent, or Firm* — Harrington & Smith

(57) ABSTRACT

An approach is provided for matching vital sign information to a concurrently recorded data set according to a time domain. The approach involves determining sensor information collected from one or more sensors configured to monitor one or more vital signs of one or more objects within a monitored area. The approach also involves processing and/or facilitating a processing of the sensor information to detect the one or more objects and to track the one or more vital signs of the one or more objects over a time domain. The approach further involves matching the one or more vital signs of the one or more objects to a concurrently recorded data set based on the time domain. The approach further involves storing at least one record of the one or more vital signs matched to the concurrently recorded data set.

19 Claims, 15 Drawing Sheets

(51) Int. Cl.
   *G01S 13/88*   (2006.01)
   *G16H 40/67*   (2018.01)
   *A61B 5/0205*  (2006.01)
   *G01S 7/41*    (2006.01)
   *A61B 5/113*   (2006.01)
   *A61B 5/05*    (2006.01)
   *A61B 5/00*    (2006.01)
   *G16H 10/60*   (2018.01)
   *A61B 5/08*    (2006.01)
   *A61B 5/024*   (2006.01)

(52) U.S. Cl.
   CPC .............. *G16H 40/67* (2018.01); *A61B 5/024* (2013.01); *A61B 5/0816* (2013.01)

(56) References Cited

U.S. PATENT DOCUMENTS

| | | | |
|---|---|---|---|
| 2008/0077015 A1 | 3/2008 | Boric-Lubecke et al. | 600/453 |
| 2010/0152600 A1* | 6/2010 | Droitcour | A61B 5/05 600/534 |
| 2013/0002434 A1 | 1/2013 | Cuddihy et al. | 340/573.7 |
| 2013/0300573 A1 | 11/2013 | Brown et al. | 340/870.01 |

* cited by examiner

FIG. 2A
FIG. 2B
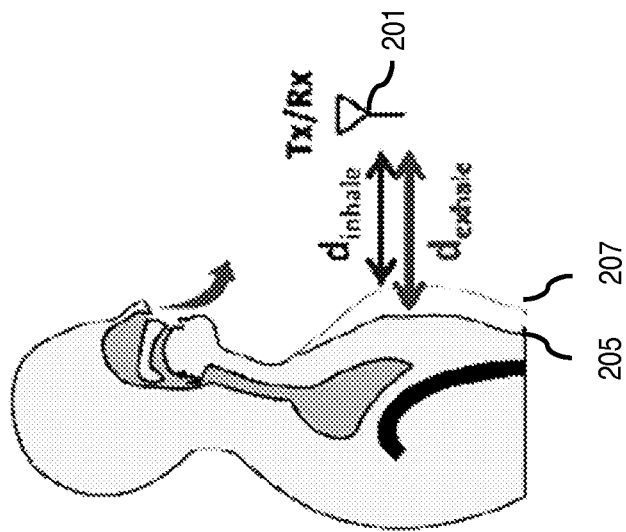
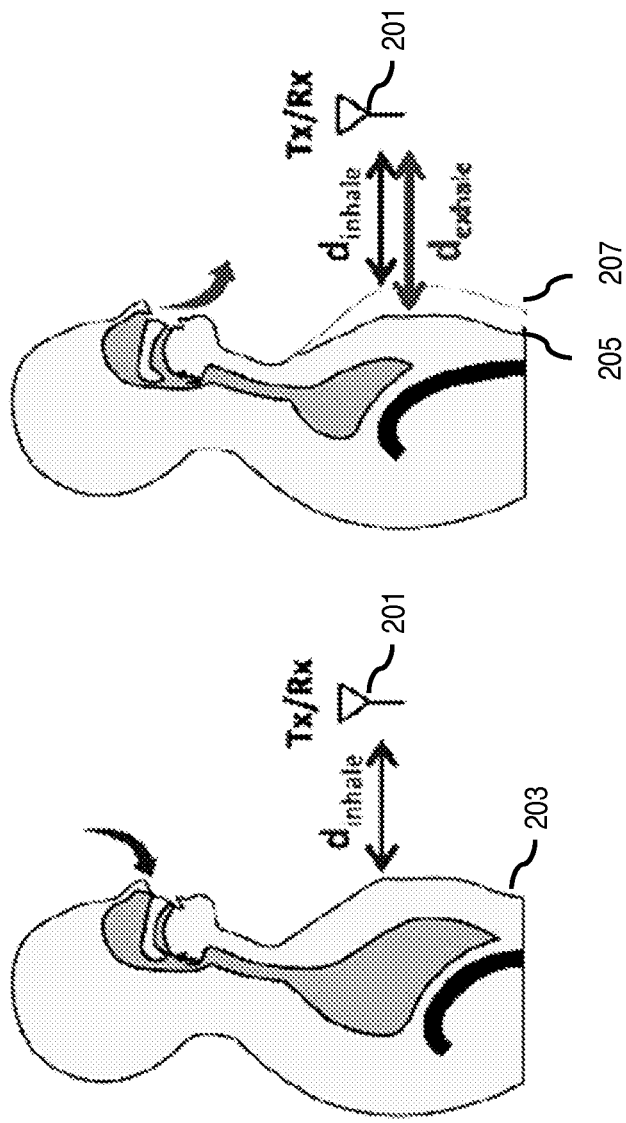

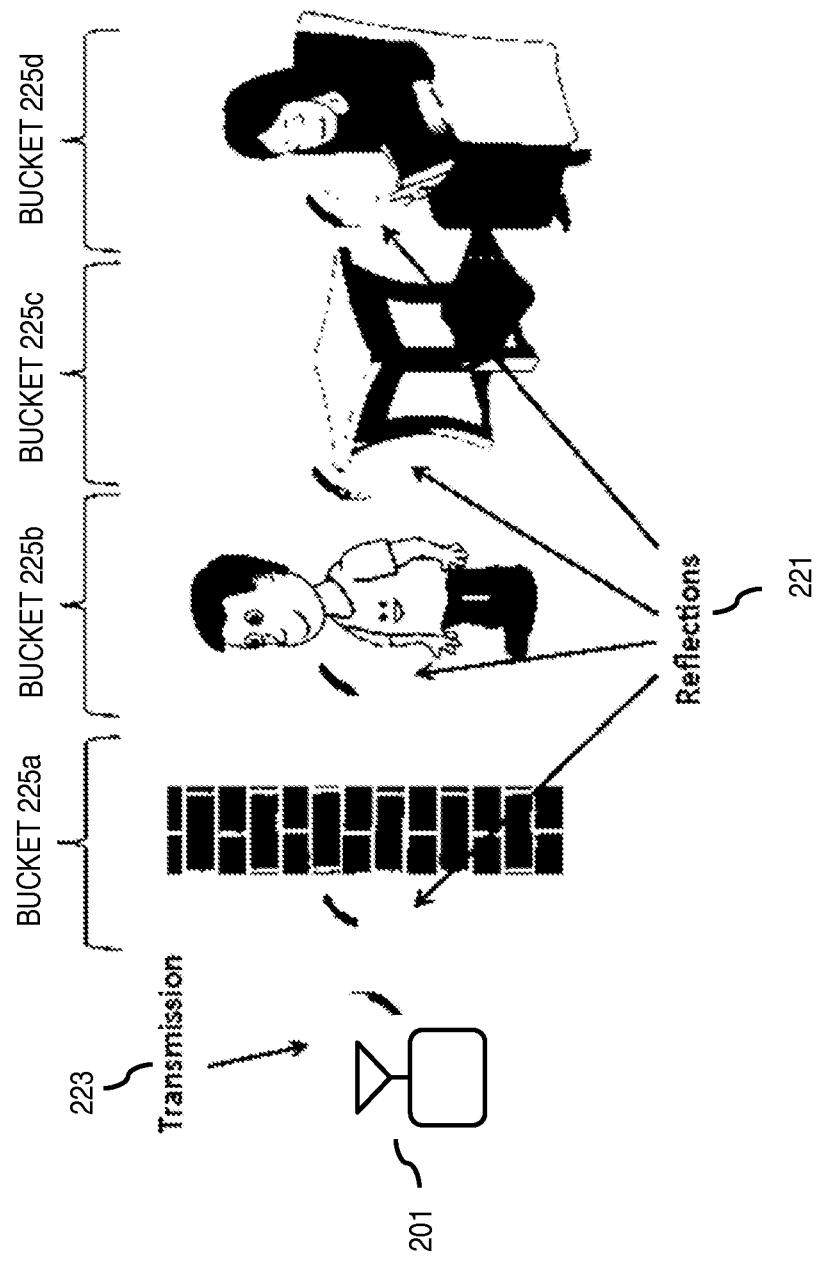

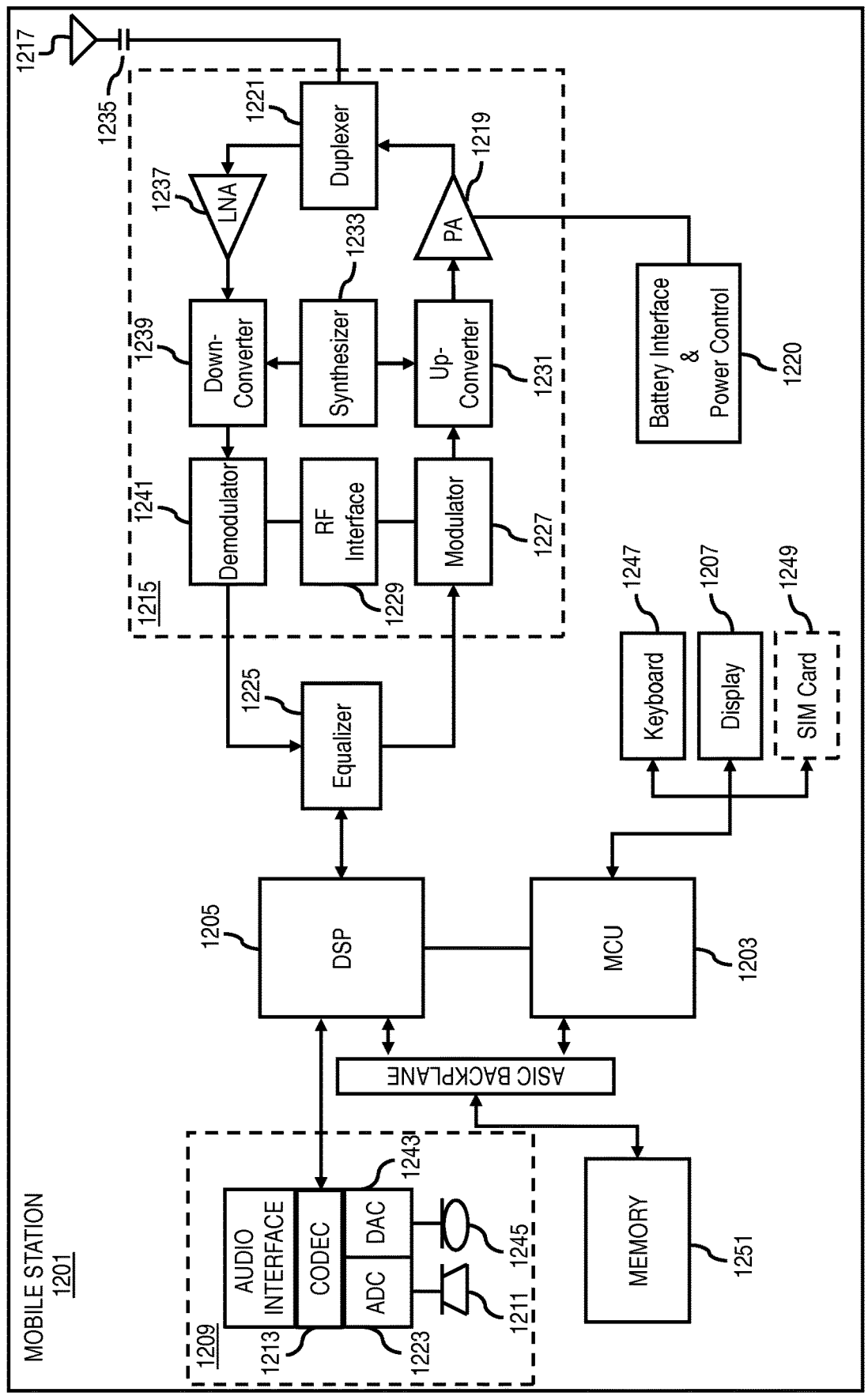

METHOD AND APPARATUS FOR MATCHING VITAL SIGN INFORMATION TO A CONCURRENTLY RECORDED DATA SET

This patent application is a U.S. National Stage application of International Patent Application Number PCT/FI2016/050347 filed May 20, 2016, which is hereby incorporated by reference in its entirety.

BACKGROUND

With an ever expanding availability of sensors that are capable monitoring user activity and condition, service providers are continually challenged to deliver new personalized experiences based on these sensors. For example, health sensors capable of monitoring vital signs from both human and non-human objects are growing in popularity. The vital sign information generated by these sensors can potentially provide highly specific information for personalizing services to enhance a user's experience, particularly as they consume or otherwise use the services (e.g., personalize media recommendations based on vital sign information collected while consuming media within a media service). As a result, service providers face significant technical challenges in correlating sensor-based vital sign information with user consumption of services or applications.

SOME EXAMPLE EMBODIMENTS

Therefore, there is a need for an approach for providing vital sign information matching to a concurrently recorded data set.

According to one embodiment, a method comprises determining sensor information collected from one or more sensors configured to monitor one or more vital signs of one or more objects within a monitored area. The method also comprises processing and/or facilitating a processing of the sensor information to detect the one or more objects and to track the one or more vital signs of the one or more objects over a time domain. The method further comprises matching the one or more vital signs of the one or more objects to a concurrently recorded data set based on the time domain. The method further comprises storing at least one record of the one or more vital signs matched to the concurrently recorded data set.

In another embodiment, the one or more sensors are further configured to monitor one or more locations of the one or more objects, and the sensor information includes the one or more locations. The method then further comprises matching the one or more locations of the one or more objects to the concurrently recorded data set based on the time domain, and storing the one or more locations matched according to the time domain in the at least one record.

In yet another embodiment, the method further comprises determining identification information for the one or more objects based on the sensor information, the one or more vital signs, profile information associated with the one or more objects, or a combination thereof, and storing the identification data in the at least one record.

In yet another embodiment, the method further comprises providing an access to the at least one record to at least one application process. The application process then reads the data from the record and performs one or more actions based on the at least one record.

According to another embodiment, an apparatus comprises at least one processor, and at least one memory including computer program code for one or more computer programs, the at least one memory and the computer program code configured to, with the at least one processor, cause, at least in part, the apparatus to determine sensor information collected from one or more sensors configured to monitor one or more vital signs of one or more objects within a monitored area. The apparatus is also caused to process and/or facilitate a processing of the sensor information to detect the one or more objects and to track the one or more vital signs of the one or more objects over a time domain. The apparatus is further caused to match the one or more vital signs of the one or more objects to a concurrently recorded data set based on the time domain. The apparatus is further caused to store at least one record of the one or more vital signs matched to the concurrently recorded data set.

In another embodiment, the one or more sensors are further configured to monitor one or more locations of the one or more objects, and the sensor information includes the one or more locations. The apparatus is then further caused to match the one or more locations of the one or more objects to the concurrently recorded data set based on the time domain, and store the one or more locations matched according to the time domain in the at least one record.

In yet another embodiment, the apparatus is further caused to determine identification information for the one or more objects based on the sensor information, the one or more vital signs, profile information associated with the one or more objects, or a combination thereof, and storing the identification data in the at least one record.

In yet another embodiment, the apparatus is further caused to provide an access to the at least one record to at least one application process. The application process then reads the data from the record and performs one or more actions based on the at least one record.

According to another embodiment, a computer-readable storage medium carries one or more sequences of one or more instructions which, when executed by one or more processors, cause, at least in part, an apparatus to process and/or facilitate a processing of image data associated with at least one image to determine sensor information collected from one or more sensors configured to monitor one or more vital signs of one or more objects within a monitored area. The apparatus is also caused to process and/or facilitate a processing of the sensor information to detect the one or more objects and to track the one or more vital signs of the one or more objects over a time domain. The apparatus is further caused to match the one or more vital signs of the one or more objects to a concurrently recorded data set based on the time domain. The apparatus is further caused to store at least one record of the one or more vital signs matched to the concurrently recorded data set.

In another embodiment, the one or more sensors are further configured to monitor one or more locations of the one or more objects, and the sensor information includes the one or more locations. The apparatus is then further caused to match the one or more locations of the one or more objects to the concurrently recorded data set based on the time domain, and store the one or more locations matched according to the time domain in the at least one record.

In yet another embodiment, the apparatus is further caused to determine identification information for the one or more objects based on the sensor information, the one or more vital signs, profile information associated with the one or more objects, or a combination thereof, and storing the identification data in the at least one record.

In yet another embodiment, the apparatus is further caused to provide an access to the at least one record to at least one application process. The application process then reads the data from the record and performs one or more actions based on the at least one record.

According to another embodiment, an apparatus comprises means for determining sensor information collected from one or more sensors configured to monitor one or more vital signs of one or more objects within a monitored area. The apparatus also comprises means for processing and/or facilitating a processing of the sensor information to detect the one or more objects and to track the one or more vital signs of the one or more objects over a time domain. The apparatus further comprises means for matching the one or more vital signs of the one or more objects to a concurrently recorded data set based on the time domain. The apparatus further comprises means for storing at least one record of the one or more vital signs matched to the concurrently recorded data set.

In another embodiment, the one or more sensors are further configured to monitor one or more locations of the one or more objects, and the sensor information includes the one or more locations. The apparatus then comprises means for matching the one or more locations of the one or more objects to the concurrently recorded data set based on the time domain, and storing the one or more locations matched according to the time domain in the at least one record.

In addition, for various example embodiments of the invention, the following is applicable: a method comprising facilitating a processing of and/or processing (1) data and/or (2) information and/or (3) at least one signal, the (1) data and/or (2) information and/or (3) at least one signal based, at least in part, on (or derived at least in part from) any one or any combination of methods (or processes) disclosed in this application as relevant to any embodiment of the invention.

For various example embodiments of the invention, the following is also applicable: a method comprising facilitating access to at least one interface configured to allow access to at least one service, the at least one service configured to perform any one or any combination of network or service provider methods (or processes) disclosed in this application.

For various example embodiments of the invention, the following is also applicable: a method comprising facilitating creating and/or facilitating modifying (1) at least one device user interface element and/or (2) at least one device user interface functionality, the (1) at least one device user interface element and/or (2) at least one device user interface functionality based, at least in part, on data and/or information resulting from one or any combination of methods or processes disclosed in this application as relevant to any embodiment of the invention, and/or at least one signal resulting from one or any combination of methods (or processes) disclosed in this application as relevant to any embodiment of the invention.

For various example embodiments of the invention, the following is also applicable: a method comprising creating and/or modifying (1) at least one device user interface element and/or (2) at least one device user interface functionality, the (1) at least one device user interface element and/or (2) at least one device user interface functionality based at least in part on data and/or information resulting from one or any combination of methods (or processes) disclosed in this application as relevant to any embodiment of the invention, and/or at least one signal resulting from one or any combination of methods (or processes) disclosed in this application as relevant to any embodiment of the invention.

In various example embodiments, the methods (or processes) can be accomplished on the service provider side or on the mobile device side or in any shared way between service provider and mobile device with actions being performed on both sides.

For various example embodiments, the following is applicable: An apparatus comprising means for performing the method of any of the claims.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The embodiments of the invention are illustrated by way of example, and not by way of limitation, in the figures of the accompanying drawings:

FIGS. 2A-2E are diagrams illustrating a process for using sensors employing a radio signal reflection measurement technology for determining vital sign information and location information for one or more objects, according to various embodiments;

FIG. 12 is a diagram of a mobile terminal (e.g., handset) that can be used to implement an embodiment of the invention.

DESCRIPTION OF SOME EMBODIMENTS

Examples of a method, apparatus, and computer program for matching vital sign information to a concurrently recorded data set according to a time domain are disclosed.

In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention. Although various embodiments are described with respect to automated classification of images based on fogging attributes, it is contemplated that the approach described herein may be applicable to any other condition or feature that can potentially affect or degrade image quality. For example, the embodiments described herein can be practiced with any opacity attribute (e.g., lens flaring, temporary obstructions, etc.) that can interfere or obscure an image or portion of an image in place of the fogging attribute.

Figure 1:
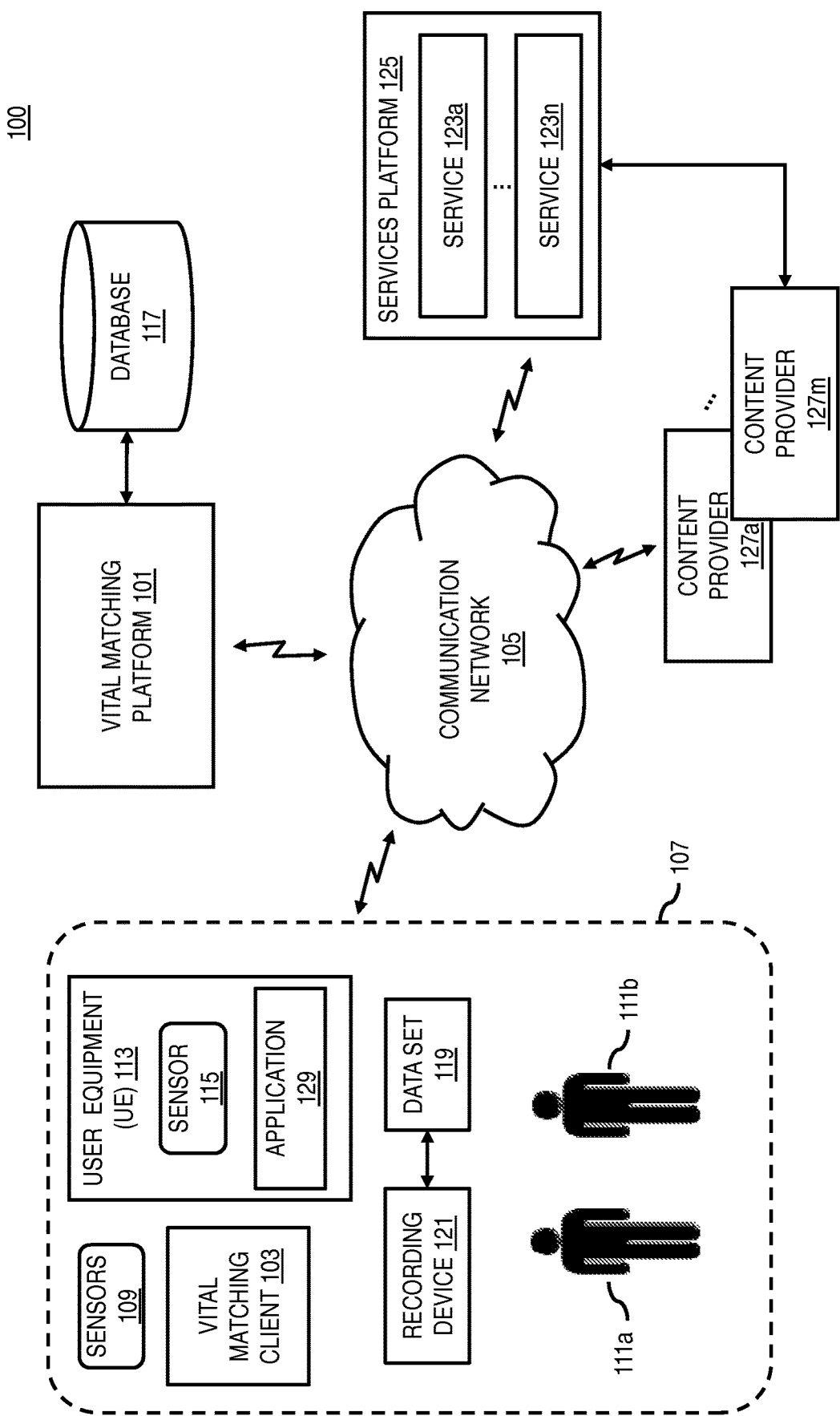
FIG. 1 is a diagram of a system capable of matching vital sign information to a concurrently recorded data set according to a time domain, according to one example embodiment.

FIG. 1 is a diagram of a system capable of matching vital sign information to a concurrently recorded data set according to a time domain, according to one example embodiment. One area of interest among service providers and device manufacturers has been to provide unique and personalized experiences to their users. For example, experiences such as virtual reality and augmented reality are gaining increasing popularity and becoming available from a growing array of providers. Similarly, traditional services such as media consumption services (e.g., online video and/or music services) are available from a wide array of providers. Accordingly, one way service providers attempt to differentiate themselves is by finding new ways to fine tune or personalize their services to individual users. However, to provide something new for users, there also is a need for gathering more information about users as they interact with the services. This information, for instance, can then be used to infer user preferences, behaviors, etc. with respect to a concurrently recorded data set (e.g., recorded media, virtual reality experience, etc.) offered by a particular service to personalize the services to an individual user.

To address the problem or need for gathering more information about users, a system 100 of FIG. 1 introduces a capability to use sensors that are capable of monitoring the vital signs and, optionally, locations of objects that produce vital signs (e.g., living human or non-human subjects as opposed to inanimate objects) within a monitored area and then to match the monitored vital signs and/or locations of the objects to a concurrently recorded data set (e.g., recorded media) depicting the objects as they are experiencing or consuming a service or application. In one embodiment, the concurrently recorded data set can be captured using a camera or other media capturing device associated with the monitored area. For example, video recording of the monitored area can be performed using 360 degree view cameras, three-dimensional cameras, and/or other presence capture cameras. The video files produced by these cameras can then be used as the recorded media or data set described in the various embodiments discussed herein.

In one embodiment, the system 100 then creates a record of the matched vital sign and location information to store in or otherwise associate with the concurrently recorded data set. The system 100, for instances, matches the vital sign information/location information of the detected with the recorded data according to a time domain, so that the vital sign information is synchronized in time with the data set. In one embodiment, the record and its associated recorded media or data set can be referred to as "vital media" to indicate that the recorded media includes vital information and/or location tracking information for objects 111 (e.g., subjects) matched to the time domain of the media. In other words, the vital media matches vital sign information and/or location tracking information to the recorded media to capture a record that correlates the vital sign information/location to what is happening in the recorded media.

In one embodiment, the vital sign information/location information record and/or data set is then made available to various applications and/or services, which can take advantage of the recorded information to further personalize their respective services or to perform unique actions based on the matched vital sign/location information.

As shown in FIG. 1, in one embodiment, the system 100 comprises a vital matching platform 101 with connectivity to a vital matching client 103 over a communication network 105. The vital matching platform 101 (e.g., a server component) and the vital matching client 103 (e.g., a local client component) can operate in combination or individually to provide matching of vital sign information to a concurrently recorded data set according to a time domain as described in the various embodiments discussed herein. In one embodiment, the vital matching client 103 can be associated with a monitored area 107 configured with one or more sensors 109 to monitor vital sign information and location information of one or more objects (e.g., objects 111a and 111b, also collectively referred to as objects 111) within the monitored area 107.

By way of example, the monitored area 107 is an extent of an area (e.g., indoor area and/or outdoor area) within a sensing range of the sensors 109. For example, multiple sensors 109 can be configured to provide coverage of an extended area if the monitored area 107 is beyond the coverage of a single sensor 109. In one embodiment, as previously discussed, the objects 111 are capable of producing vital signs and can be either human or non-human living subjects.

In one embodiment, the monitored area 107 may be contained within a "smart house" or "smart building" in which sensors 109 are installed to collect sensor information about the condition of the house or building and/or the occupants (e.g., objects 111) within the building or house. Accordingly, the sensors 109 and/or the vital matching client 103 can be a component of or otherwise integrated within a smart appliance or other whole house sensor system (e.g., alarm systems, home networking equipment, etc.) installed in the house or building.

In one embodiment, the sensors 109 include sensors capable of detecting vital signs with radio reflection technology. One example of this technology, known in the art, enables the sensor to monitor vital signs (e.g., heart rate, respiration rate, etc.) remotely, i.e., without requiring any physical contact between the sensors 109 and the bodies of the objects 111 (e.g., living human and/or non-human subjects) being monitored. This example technology that can be used in one embodiment, is described in more detailed with respect to FIGS. 2A-2E, which are diagrams illustrating a process for using sensors employing a radio signal reflection measurement technology for determining vital sign information and/or location information for one or more objects.

As illustrated in FIGS. 2A and 2B, a radio signal reflection-based sensor 201 can measure vital signs by determining changes in signal reflection times to a monitored object 111 (e.g., the body 203) as the object 111 moves in response to breathing or a beating heart. For example, FIGS. 2A and 2B respectively illustrate movements of the body 203 during a typical inhale position (FIG. 2A) and an exhale position (FIG. 2B) of a breathing cycle. As shown in FIG. 2A, the sensor 201 transmits a radio towards the body 203 and measures when a reflected or return signal is received at that sensor 201 to determine a signal reflection time as an estimate of the distance from the sensor 201 to the body 203 at an inhale position.

Figure 2C:
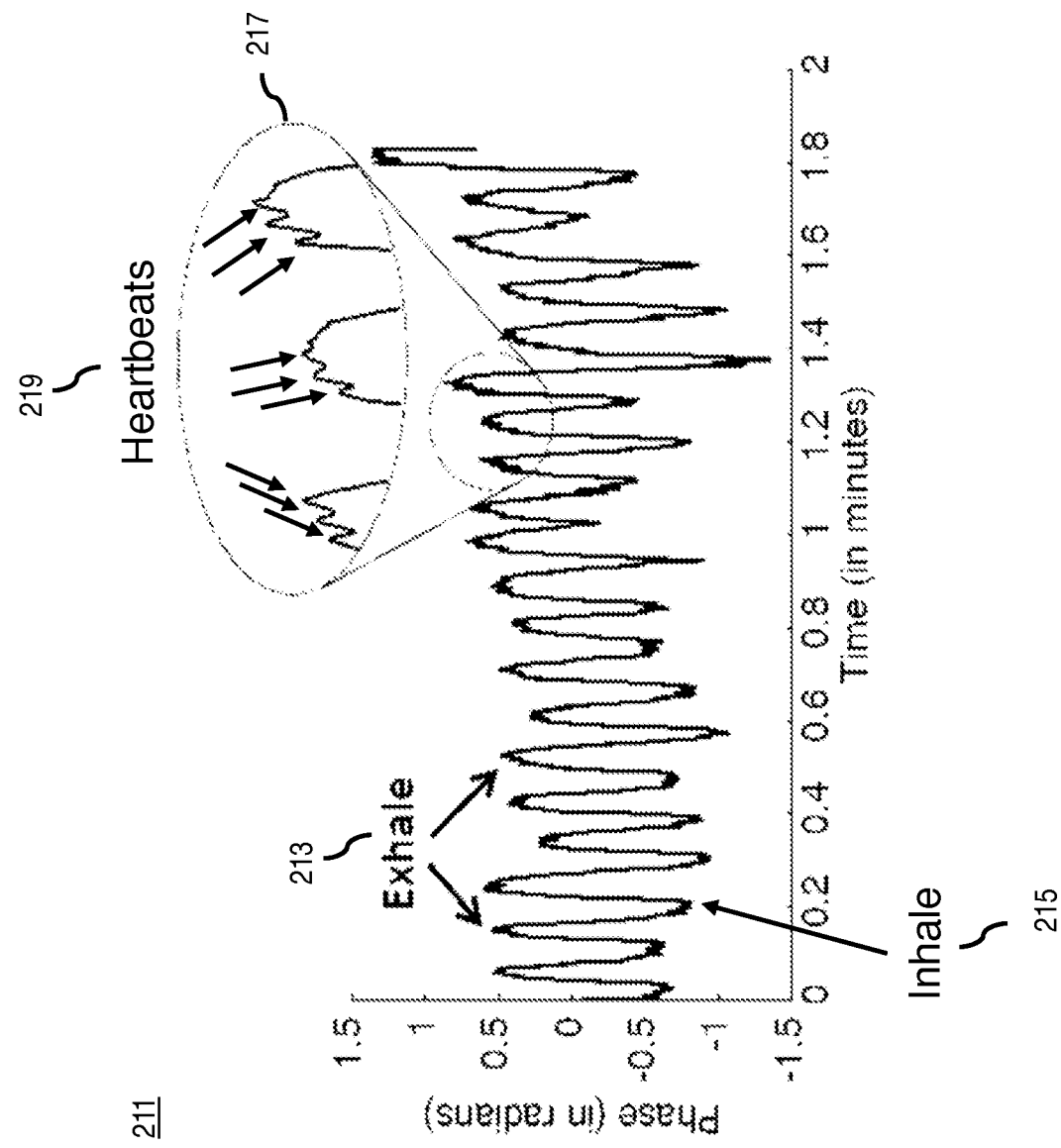

FIG. 2B illustrates a continuation of the signal reflection time measurement over time as the body 203 changes from an inhale position 205 to an exhale position 207. The difference in the position of the chest surface of the body 203 is detectable as a difference in the signal reflection time collected during the movement. This leads to a measurable variation to the received signal as shown in FIG. 2C, which illustrates a chart 211 of phase variations in the reflected signal as received at the sensor 201 over time. The phase variation, for instance, is function of the distance variation between the sensor and the body 203 caused by breathing and/or heartbeat movements. For example, breathing movements result in exhale peaks 213 and inhale valleys 215 in chart. Counting the peaks 213 and/or valleys 215 over a period of time then results in measuring a respiration or breathing rate of the object or body 203 to provide respiration rate as one vital sign measurement.

Because heartbeat movements are relatively minute compared with body movements caused by breathing, the phase variations resulting from heartbeats of the body 203 can be more easily seen in the chart 211 in an exploded view 217. Similar to the peaks 213 and valleys 215 of the breathing movements, the heartbeats 219 also exhibit peaks and valleys that can be counted to measure a heart rate of the object 111 or body 203 as another vital sign measurement.

In one embodiment, as shown in FIG. 2D, the sensor 201 can track multiple objects 111 or subjects and their respective vital sign information within the monitored area 107. In other words, the sensor 201 can detect the presence and/or movements of the multiple objects 111 within an area simultaneously, and then concurrently, determine the vital signs associated with each of the multiple objects 111. For example, objects 111a and 111b can be distinctly determined from each other, and the respective vital sign information and/or location information determined from the sensor information of the sensors 109 can be associated with each individual object 111a and 111b. In one embodiment, the sensor 201 can use a radar technique based on Frequency Modulated Carrier Waves (FMCW) to differentiate signal reflections 221 arriving from different objects present within its monitoring area based on signal transmission 223. For example, the sensor 201 can use FMCW to separate the reflections 221 into different buckets 225a-225d depending on the distance between the objects and the sensor 201.

The discussion of the radio reflection measurement sensor of FIGS. 2A-2D are provided by way of summary and illustration of one example technology available in the art. Additional details of this technology can be found in, for instance, Fadel Adib et al., "Smart Homes that Monitor Breathing and Heart Rate," ACM CHI 2015.

Figure 2E:
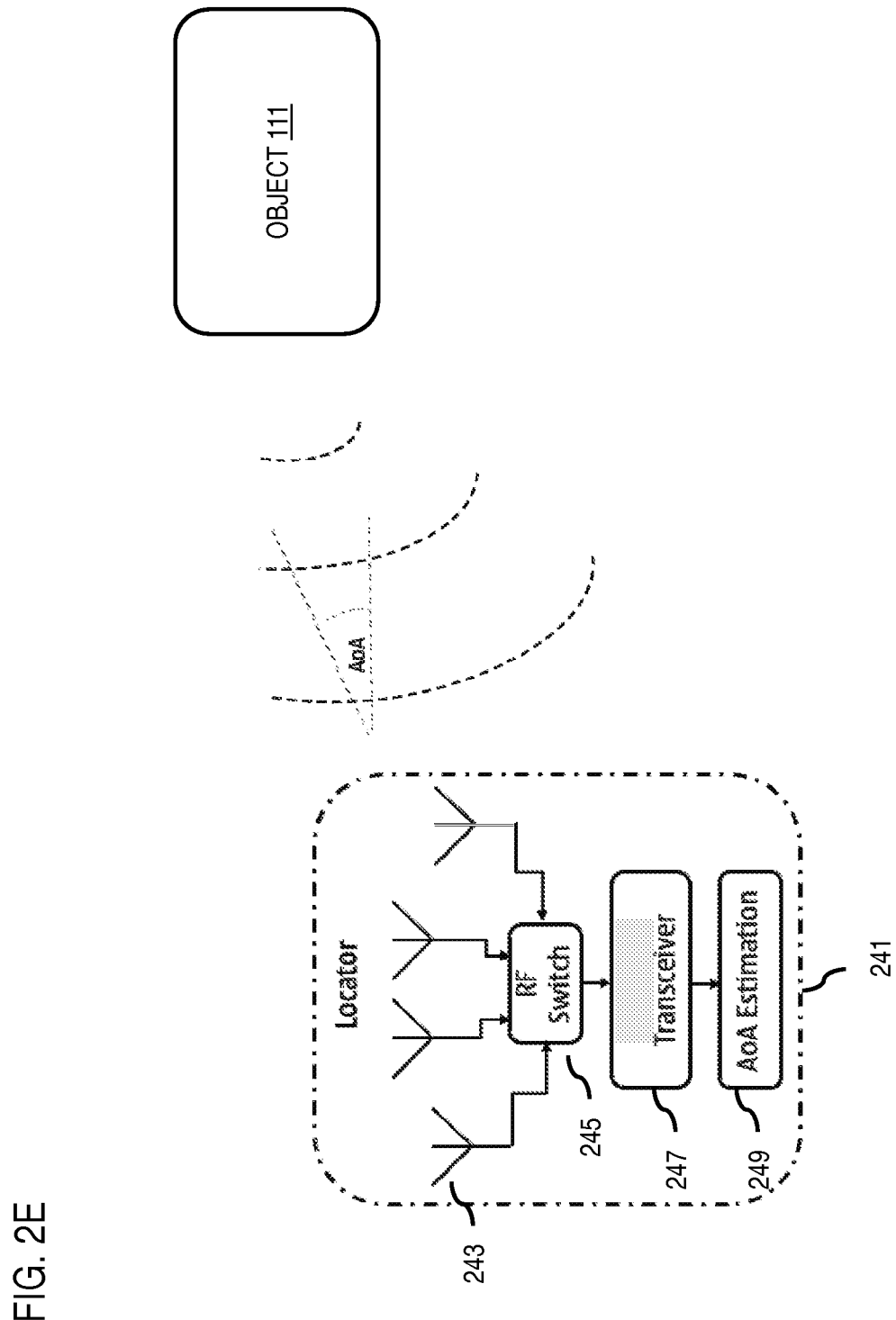

As shown in FIG. 2E, in one embodiment, the sensors 109 can employ directional radio detection technology to facilitate determining location information for tracked objects 111. By way of example, direction estimation of the signal source from the received signal can be based on now angle-of-arrival (AoA) estimation techniques. For example, such an AoA technique can be based on a receiver 241 (e.g., a sensor 109) having multiple antennas 243 connected via a Radio Frequency (RF) Switch 245 to a transceiver 247 (e.g., for controlling signal transmission) and an AoA estimation unit 249 (e.g., for processing returned signal copies to estimate the AoA).

In one embodiment, the estimation of the AoA is based on the measured time difference of signal copies (e.g., transmitted by multiple physically separated antennas 243) reflected from the object 111. The time difference between the received reflected signal copies is due, for instance, to variable propagation channel lengths, and the practical estimation is typically based on secondary effects to the signal, such as the resulting phase difference of the signal copies. In one embodiment, the sensor receiver device 241 scans for AoA packets in the signal reflected from the object 111 and executes amplitude and phase sampling during reception of these packets. The receiver 241 may then use the amplitude and phase samples, along with its own antenna array information, to estimate the AoA of the packet from the signal copies reflected from the object 111.

Although the sensors 109 of FIG. 1 are described as using non-contact or remote sensing technologies (e.g., radio reflection measurement technology), it is contemplated that any non-contact or contact sensor type can be used according to the various embodiments described herein. For example, the system 100 may employ a combination of contact and/or non-contact sensors 109 to determine any combination of vital signs and/or locations of tracked subjects, provided that the collected vital sign information and/or location information are mapped to a time domain. In other words, the sensors 109 capture the time at which a particular vital sign or location measurement is made for a particular subject. For example, the system 100 can employ one sensor 109 that uses radio reflection measurement technology to detect multiple objects 111 and track their respective locations over time, while using wearable (contact) sensors 109 on each object 111 to measure vital signs produced by the objects 111.

Returning to FIG. 1, in one embodiment, user equipment 113 configured with respective sensors 115 can be used in place of or in addition to the sensors 109 and/or vital matching client 103 associated with a monitored area 107.

In one embodiment, after collecting and processing sensor information from the sensors 109 to detect or identify objects producing vital signs (e.g., using the radio reflection measurement technology), the vital matching platform 101 creates a record or file of the vital sign information along with associated time domain (e.g., time of vital sign and/or location measurement). In one embodiment, the vital sign information record can be stored in, for instance, the database 117. By way of example, the record or file may consist of one or more information fields based on object detection including, but not limited to: (1) time; (2) object identification—can be, e.g., a real identification such as object name, or can be an anonymous or random identifier; (3) vital sign information—heart rate, respiration rate, etc.; and (4) object location information—indicated, e.g., by an object range, object direction—elevation and azimuth, received signal strength indication (RSSI), etc. from the sensor 109 as described above. Table 1 illustrates an example of the record or file content. It is noted that although Table 1 depicts a record including both vital sign information and location information, in one embodiment, the location information need not be included.

TABLE 1

| Time | Identity | Heart rate | Range | Elevation angle | Azimuth angle | RSSI |
|---|---|---|---|---|---|---|
| 00:00:134 | Obj 1 | 60 | 3.2 m | 176° | 281° | −73 dBm |
| 00:01:023 | Obj 2 | 83 | 2.0 m | 145° | 13° | −60 dBm |

TABLE 1-continued

| Time | Identity | Heart rate | Range | Elevation angle | Azimuth angle | RSSI |
|---|---|---|---|---|---|---|
| 00:01:345 | Obj 1 | 62 | 3.0 m | 176° | 281° | −73 dBm |
| 00:01:355 | Obj 2 | 82 | 2.0 m | 145° | 14° | −62 dBm |
| 00:01:365 | Obj 2 | 85 | 2.2 m | 145° | 17° | −65 dBm |
| 00:01:375 | Obj 2 | 83 | 2.1 m | 145° | 19° | −62 dBm |
| 00:01:385 | Obj 1 | 61 | 2.8 m | 176° | 281° | −73 dBm |
| 00:01:395 | Obj 2 | 85 | 2.2 m | 145° | 22° | −63 dBm |
| 00:01:953 | Obj 2 | 80 | 2.4 m | 145° | 21° | −62 dBm |
| 00:02:078 | Obj 1 | 65 | 2.5 m | 176° | 281° | −73 dBm |

In one embodiment, the objects 111 may be identified or detected, for example, based on sensor information received from the sensors 109 (e.g., radio reflection measurement sensors and/or AoA sensors). As shown in Table 1 above, the objects may be identified using an anonymous or random identifier (e.g., "Obj 1" or "Obj 2") without reference to a real or actual identifier of the object 111. Alternatively, the objects 111 can be identified using a real identifier (e.g., a name). In one embodiment, the AoA radio signal or other signal used by the sensors 109 may include, for example, a name of the user of the device (e.g., if the user is associated with, e.g., the UE 113). In another embodiment, unique patterns in the vital signs (e.g., heart beat pattern) can be compared or matched against a database of known data (e.g., heart beat patterns) to identify the object 111. In yet another embodiment, the object identification may also be based on, for example, face detection if the recorded media (a data set 119) includes video or images (e.g., captured via a recording device 121, e.g., a camera device, available in the monitored area 107), and/or voice detection if the recorded media includes audio samples. In one embodiment, tracking of the object may be based on vital signs if facial recognition is unavailable (e.g., faces not always visible, or become visible only after starting of a recording of the data set 119).

In one embodiment, the vital matching platform 101 can match the record or file against the data set 119 that is concurrently recorded while the vital sign and/or location information of the tracked objects 111 is collected. For example, the data set 119 can include recorded media (video and/or audio) of a user while the user is engaged in a service activity (e.g., watching a video, playing a game, experiencing a virtual reality or augmented reality environment, etc.) or some other monitored activity or situation. In one embodiment, although the recorded media or data set 119 is described as an audio or video recording, it is also contemplated that the data set 119 can also be any time-based data set associated with a service or application. For example, time-based data can be a data sequence arranged according to a time domain so that a time correlation can be made between time-coded measurements of vital signs and/or locations against the time-coded items in the data set. In one embodiment, the data set 119, at a minimum, can include just a series of time stamps or time codes with no other information field.

In one embodiment, the service activity or monitoring activity can be associated with one or more services 123a-123n (also collectively referred to as services 123) of the services platform 125 and/or the content providers 127a-127m (also collectively referred to as content providers 127). In one embodiment, the recorded media (e.g., the data set 119) can be captured by the UE 113 and/or the vital matching client 103. In one embodiment, as with the record, the data set 119 can be stored in the database 117.

In one embodiment, the record of the matched vital-sign information, location information, and/or the data set 119 (e.g., concurrently recorded media) can be provided to or otherwise made available (e.g., by granting access to) the service 123 and/or services platform 125 to support one or more application processes (e.g., an application 129 executed by the UE 113).

For example, one example use case for the matched vital sign information record and data set 119 can be for a service 123 that monitors reactions for a group of people where reactions within the group can be different based on each group member's position. The service 123, for instance, can use the record to monitor audience reactions in a theatrical performance based on where the audience members are sitting. The capability of the system 100 to remotely monitor and individually track multiple people at the same time advantageously enables the service 123 to more efficiently and quickly set up a monitored area 107 without having to individually profile or equip each member with individual sensors.

In another example use case, a service 123 can use the system 100 to performed health-based monitoring of people inside a home (e.g., monitoring elderly or sick people). The system 100 can track and record the movements and vital signs of the people inside in the house using the embodiments discussed above and then make decisions or initiate actions based on the matched vital sign information record and/or the data set 119. For example, based on the movement and vital signs of the tracked people, their health conditions can be evaluated. For example, if the vital sign and location record indicates a person is breathing but has stayed stationary for more than 20 hours, the service 123 can initiate a health alert or otherwise send a notification to interested parties.

In yet another example use case, a service 123 can provide emergency responders with location tracking information and vital sign information of subjects at a location of a known emergency (e.g., a location at which a fire alarm has been activated).

It is noted that the example use cases discussed herein is provided by way of illustration and not limitation. It is contemplated that the matched vital sign/location record and/or data set 119 can be provided to any type of service or application.

In one embodiment, the UE 113 may include, but is not restricted to, any type of a mobile terminal, wireless terminal, fixed terminal, or portable terminal. Examples of the UE 113, may include, but are not restricted to, a mobile handset, a wireless communication device, a station, a unit, a device, a multimedia computer, a multimedia tablet, an Internet node, a communicator, a desktop computer, a laptop computer, a notebook computer, a netbook computer, a tablet computer, a Personal Communication System (PCS) device, a personal navigation device, a Personal Digital Assistant (PDA), a digital camera/camcorder, an infotainment system, a dashboard computer, a television device, or any combination thereof, including the accessories and peripherals of these devices, or any combination thereof. In one embodiment, the UE 113 may support any type of interface for supporting the presentment of one or more recommended routes towards at least one destination. In addition, the UE 113 may facilitate various input means for receiving and generating information, including, but not restricted to, a touch screen capability, a keyboard and keypad data entry, a voice-based input mechanism, and the like. Any known and future implementations of the UE 113 may also be applicable. In one embodiment, the UE 113 may be included, embedded within, or communicatively connected to a building, structure, vehicle, etc.

The UE 113 may further include applications 129. Further, the applications 129 may include various applications such as, but not restricted to, location-based service application, navigation application, content provisioning application, camera/imaging application, mapping application, sensor monitoring applications, media player application, social networking application, calendar applications, multimedia application, and the like.

The UE 113 can also include one or more sensors 115, which can be implemented, embedded or connected to the UE 113 and/or the monitored area 107. The sensors 115 may be any type of sensor. In certain embodiments, the sensors 115 may include, for example, but not restricted to, a global positioning sensor for gathering location data, such as a Global Navigation Satellite System (GNSS) sensor, a network detection sensor for detecting wireless signals or receivers for different short-range communications (e.g., Bluetooth, Wi-Fi, Li-Fi, Near Field Communication (NFC) etc.), temporal information sensors, a camera/imaging sensor for gathering image data (e.g., the camera sensors may automatically capture images of various location for analysis purpose), and the like. In another embodiment, the sensors 115 may include light sensors, orientation sensors augmented with height sensor and acceleration sensor (e.g., an accelerometer can measure acceleration and can be used to determine orientation of the UE 113), tilt sensors, e.g., gyroscopes, to detect the degree of incline or decline of the vehicle along a path of travel, an electronic compass to detect a compass direction, moisture sensors, pressure sensors, etc.

Further, various elements of the system 100 may communicate with each other through a communication network 105. The communication network 105 of system 100 includes one or more networks such as a data network, a wireless network, a telephony network, or any combination thereof. It is contemplated that the data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular communication network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (Wi-Fi), wireless LAN (WLAN), Bluetooth®, Internet Protocol (IP) data casting, satellite, mobile ad-hoc network (MANET), vehicle controller area network (CAN bus), and the like, or any combination thereof.

In one embodiment, the vital matching platform 101 may be a platform with multiple interconnected components. The vital matching platform 101 may include one or more servers, intelligent networking devices, computing devices, components and corresponding software for matching vital sign information to a concurrently recorded data set according to a time domain. In addition, it is noted that the vital matching platform 101 may be a separate entity of the system 100, a part of the one or more service 123, the services platform 125, and/or the UE 113.

The services platform 125 may include any type of service. By way of example, the services platform 125 may include mapping services/application, navigation services/application, camera/imaging application, travel planning services/application, route calculation services/application, notification services/application, social networking services/application, content (e.g., audio, video, images, etc.) provisioning services/application, application services/application, storage services/application, contextual information determination services/application, location based services/application, information (e.g., weather, news, etc.) based services/application, etc. In one embodiment, the services platform 125 may interact with the UE 113, the vital matching platform 101 and the content provider 127 to supplement or aid in the processing of the content information.

By way of example, the service 123 may be an online service that reflects interests and/or activities of users based on the matched vital sign information record and/or the data set 119. The content provider 127 may provide content to the UE 113, the vital matching platform 101, and the service 123 of the services platform 125. The content provided may be any type of content, such as, image content, textual content, audio content, video content, etc. In one embodiment, the content provider 127 may provide content that may supplement content of the database 117, applications 129, the sensors 109, sensors 115, or a combination thereof. In one embodiment, the content provider 127 may provide or supplement the mapping services/application, navigation services/application, travel planning services/application, route calculation services/application, notification services/application, social networking services/application, content (e.g., audio, video, images, etc.) provisioning services/application, application services/application, storage services/application, contextual information determination services/application, location based services/application, information (e.g., weather, news, etc.) based services/application, local map data, or any combination thereof. In one embodiment, the content provider 127 may also store content associated with the UE 113, the vital matching platform 101, and the service 123 of the services platform 125. In another embodiment, the content provider 127 may manage access to a central repository of data, and offer a consistent, standard interface to data, such as, a repository of attributes information for one or more images, and so on. Any known or still developing methods, techniques or processes for determining attributes information for at least one image may be employed by the vital matching platform 101.

By way of example, the UE 113, the vital matching platform 101 communicate with each other and other components of the communication network 105 using well known, new or still developing protocols. In this context, a protocol includes a set of rules defining how the network nodes within the communication network 105 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application (layer 5, layer 6 and layer 7) headers as defined by the OSI Reference Model.

Figure 3:
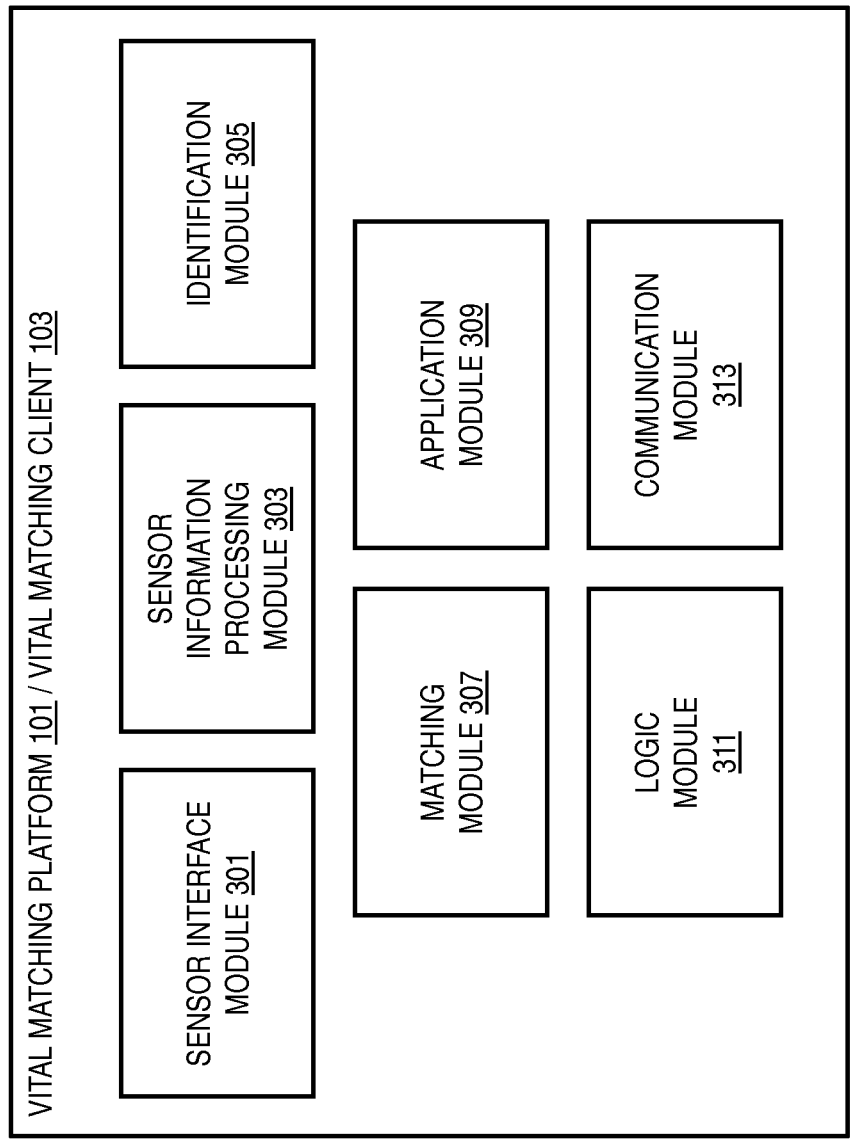
FIG. 3 is a diagram of the components of the vital matching platform, according to one example embodiment.

FIG. 3 is a diagram of the components of the vital matching platform 101 and the vital matching client 103, according to one example embodiment. By way of example, the vital matching platform 101 and the vital matching client 103, individually or in combination, may include one or more components for performing functions related to matching vital sign information to a concurrently recorded data set according to a time domain. In one embodiment, the vital matching platform 101 and/or the vital matching client 103 may include a sensor interface module 301, a sensor information processing module 303, an identification module 305, a matching module 307, an application module 309, a logic module 311, and a communication module 313. It is contemplated that the functions of these components may be combined in one or more components or performed by other components with similar functionalities. In one embodiment, any combination of modules 301-313 may be integrated in to an appliance device, networking device, or other edge device associated with the monitored area 107.

In one embodiment, the sensor interface module 301 interacts with one or more sensors 109 to initiate the collection of sensor information that indicates vital sign information and, optionally, location information for one or more objects 111 in a monitored area 107. In one embodiment, the sensor interface module 301 interacts with sensors 109 that use radio reflection measurement technology to measure vital signs produced by the objects 111 and/or the relative locations of the objects 111 to the sensors 109, as previously discussed with respect to the embodiments described herein. For example, the sensor interface module 109 can support any type of interface (e.g., wired or wireless) to interact with any number of the sensors 109 configured to monitor the objects 111. In one embodiment, the sensor information includes can include either raw or pre-processed sensor information. In addition, rather than directly interfacing with the sensors 109, the sensor interface module 301 can also retrieve the sensor information from intermediate sources (e.g., external or internal databases containing the sensor information). For example, the sensors 109 can be configured to collect the sensor information and then transmit that sensor information to a storage location (e.g., cloud or network storage). The sensor interface module 301 can then retrieve the stored sensor information from the storage location. It is further contemplated, that the sensor interface module 301 can retrieve or collect the sensor information continuously in real-time or in batches.

In one embodiment, once the sensor information is collected by the sensor interface module 301, the sensor information processing module 303 can process the sensor information to detect vital sign information and/or location information for the objects 111 according to a time domain. For example, the signal processing module can process the sensor information according to the processes described with respect to FIGS. 2A-2E to generate vital sign and/or location information matched to detected objects 111 as well as according to time.

In one embodiment, the sensor information processing module 303 can interact with the identification module 305 to provide for further identification of the detected objects 111. As previously discussed, in one embodiment, the objects 111 can be identified or otherwise labeled with a random or anonymous identifier. In another embodiment, the identification module 305 can provide for a more specific identification of the objects 111. For example, the identification module 30 can match the determined vital signs or vital sign patterns (e.g., specific breathing patterns or heart beat patterns as illustrated, for instance, in FIG. 2C) against previously stored patterns recorded for known users. The patterns can also be a combination of the actual vital signs or any other uniquely identifiable information that can be determined from the vital signs alone or in combination with the tracked location information (e.g., a certain heart rate combined with a certain respiratory rate can potentially identify a person, or the rate at which the vital signs change can also represent a pattern). If there is a match, then the identification module 305 can associate more specific identifiers (e.g., a name, a previous ID number, etc.) based on the matching. Examples of known data that can be used for this identification matching include, but are not limited to, historical data, predefined data (e.g., search for a person with certain vital sign patterns.

In one embodiment, if other information that can indicate identity is available (e.g., concurrently recorded media), the identification module 305 use the other information (e.g., other sensor information) to make or further refine an identification of the object 111. For example, if recorded media includes images or audio, the identification module 305 can process the images or audio using, for instance, facial and/or voice recognition to identify the objects depicted in the images or audio. As previously discussed, in one embodiment, the identification can be made as the information is collected or in post-processing.

In one embodiment, the sensor information processing module 303 and/or the identification module 305 can then write or store the processed sensor information into a record or file. An example of such a record is provided in Table 1 above which includes information fields indicating, e.g., time, identity, vital sign (e.g., heart rate, respiration rate, etc.), location (e.g., relative location to the sensor 109 expressed in terms of range, elevation angle, azimuth angle, and signal strength).

In one embodiment, the matching module 307 can further match the record or file generated by the sensor information processing module 303 to a data set 119 according to a time domain. For example, the data set 119 can be a concurrently made audio or video recording of the monitored area. The matching module 307, for instance, can correlate the time that a particular vital sign or location measurement was made for an object 111 with the portion of the recorded media that corresponds to the same point in time. In one embodiment, the vital sign/location information determined for the tracked objects 111 can be stored in the recorded media file or data set 119 or associated with the recorded media file or data set 119 as a separate file (e.g., as metadata associated with the recorded media file).

In one embodiment, the application module 309 then provides an application process (e.g., application 129, service 123, etc.) with access to the stored record and/or data set 119 to provide additional functionality. In general, the application process can utilize the vital sign/location information record and/or data set 119 to perform certain actions or to provide this data for certain usage based on some conditions. For example, to provide access, the application module 300 can provide the vital sign measurement and tracking information generated as described above to, e.g., a cloud server (e.g., a service 123, content provider 127, etc.). The application process can read or access this data from the cloud server to perform certain actions.

By way of example, the application processes can be used to provide any type of service or application to users based on the vital sign/location information record and/or the data set 119. For example, as previously discussed, one application can be used to track elderly or sick people in assisted or supported living conditions, where elderly and/or sick people can remain relatively independent. Another application can use the vital sign/location information record and/or data set 119 to monitor the health and track the locations of people during emergency situations to triage an emergency response. Additional details of these use cases are described in more detail below with respect to FIGS. 6-8 below.

In one embodiment, the logic module 311 may manage tasks related to matching vital information to a concurrently recorded data set, including tasks performed by the other modules. For example, although the other modules may perform their actual tasks, the logic module 311 may determine when and how those tasks are performed or otherwise direct the other modules to perform the task. In one embodiment, the logic module 311 may determine to process sensor information to track and monitor the vital signs and/or locations of monitored subjects in substantially real-time, batch mode, according to a schedule, or a combination thereof. By way of example, the schedule may be based, at least in part, on computational resources, amount of available data, etc.

The communication module 313 may be used for communication between various elements of the system 100 as well as between modules, elements, components, etc. of the classification platform 101. For example, the communication module 313 may be used to communicate commands, requests, data, etc., to/from the vital matching platform 101, database 117, the content provider 127, or the like.

The above presented modules and components of the vital matching platform 101 can be implemented in hardware, firmware, software, or a combination thereof. Though depicted as a separate entity in FIG. 1, it is contemplated that the vital matching platform 101 may be implemented for direct operation by respective UE 113, the sensors 109 (e.g., within a smart home appliance, a networking appliance, or other similar device), and/or any other component of the system 100.

Figure 4:
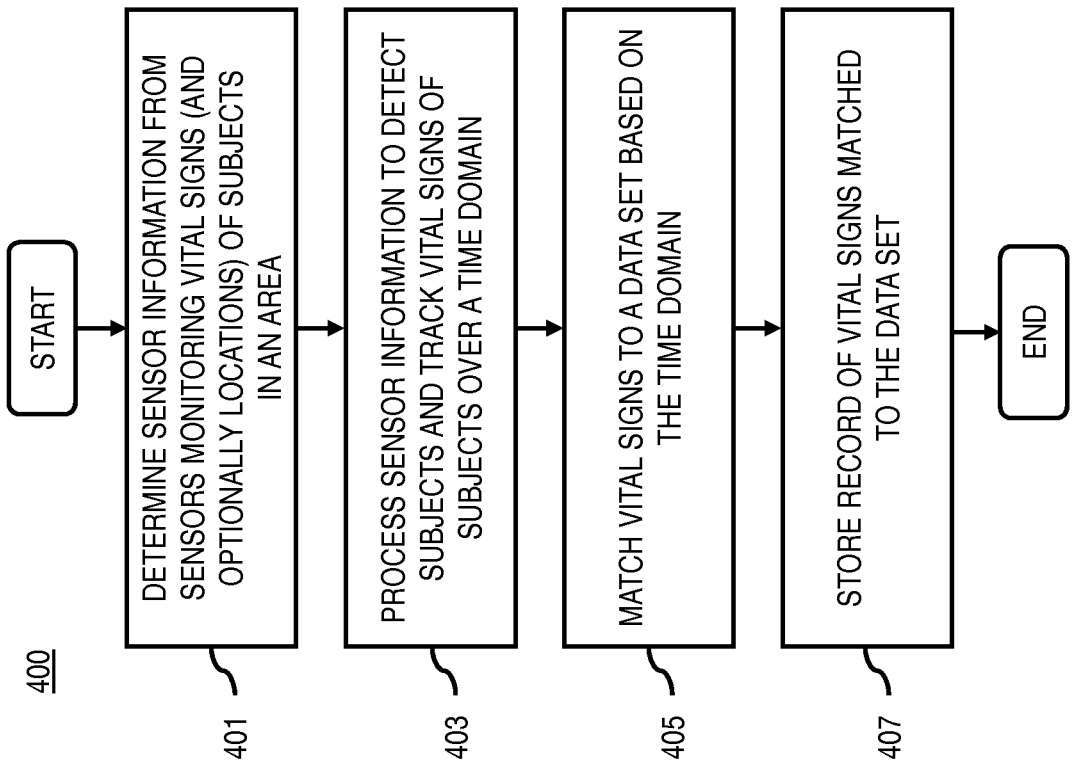
FIG. 4 is a flowchart of a process for matching vital sign information to a concurrently recorded data set according to a time domain, according to one example embodiment.
Figure 11:
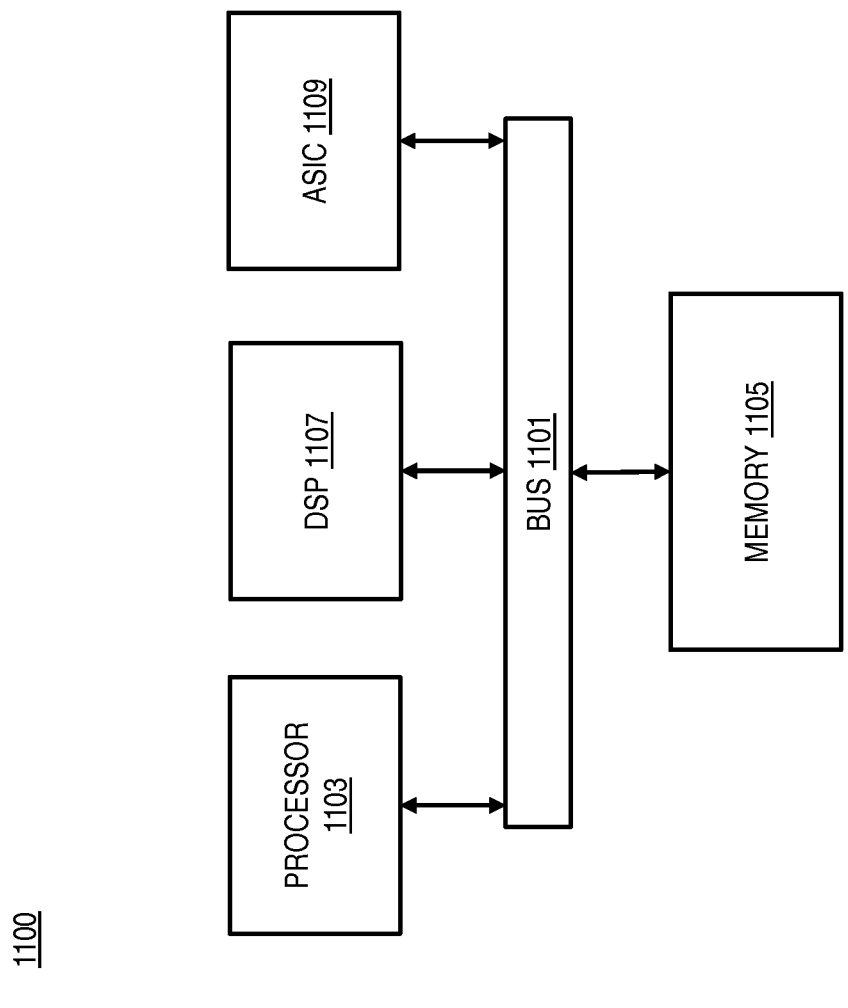
FIG. 11 is a diagram of a chip set that can be used to implement an embodiment of the invention.

FIG. 4 is a flowchart of a process for matching vital sign information to a concurrently recorded data set according to a time domain, according to one example embodiment. In one embodiment, the vital matching platform 101 performs the process 400 and is implemented in, for instance, a chip set including a processor and a memory as shown in FIG. 11. In addition or alternatively, the vital matching client 103 can perform all or a portion of the process 400.

In step 401, the vital matching platform 101 determines sensor information collected from one or more sensors configured to monitor one or more vital signs of one or more objects within a monitored area. In one embodiment, the one or more sensors are also configured to optionally monitor one or more locations of the subjects. The one or more locations then can also be included as part of the sensor information. As previously discussed, the one or more objects can be objects capable of producing vital signs (e.g., living human and non-human subjects). In one embodiment, the one or more sensors employ a radio signal reflection measurement technology to remotely determine the one or more vital signs and the one or more locations of the one or more objects. It is noted that radio signal reflection measurement sensors are discussed only as an example sensor capable of being used in the various embodiments described herein. In one embodiment, other combination of sensors (e.g., both contact and non-contact sensors) can be used to track objects and monitor their vital signs and locations over a period of time.

In step 403, the vital matching platform 101 processes and/or facilitates a processing of the sensor information to detect the one or more objects 111 and to track the one or more vital signs of the one or more objects 111 over a time domain. In other words, each measurement or reading of the vital signs and/or locations can be associated with a time stamp coinciding with the measurement time. In this way, the measurements can be correlated according to a time domain. A time domain, for instance, can be based on any clock or time sequence that common to the measurements or corresponding data.

In step 405, the vital matching platform 101 matches the one or more vital signs of the one or more objects 111 to a concurrently recorded data set 119 based on the time domain. In one embodiment, the concurrently recorded data set includes a media file that, for instance, records the objects (e.g., people) within a monitored area. As previously discussed, the recorded media can be audio or video. The vital matching platform 101 then correlates the measurement times of the vital sign and/or location measurements against the time of the recorded data set 119 or media. In this way, the media can be referred to as "vital media" which indicates that a media file or data set 119 is time matched with a concurrent vital sign and location measurements for objects 111 associated with the data set 119 or media.

In step 407, the vital matching platform 101 stores at least one record of the one or more vital signs matched to the concurrently recorded data set. In one embodiment, if the one or recorded data set is a media file, the vital matching platform 101 stores the at least one record in the media file or as metadata associated with the media file. An example format of the record or file is presented in Table 1. However, it is contemplated that any format or any set of data fields may be included in the record or file sufficient to describe time, vital sign, and location of tracked objects 111.

Figure 5:
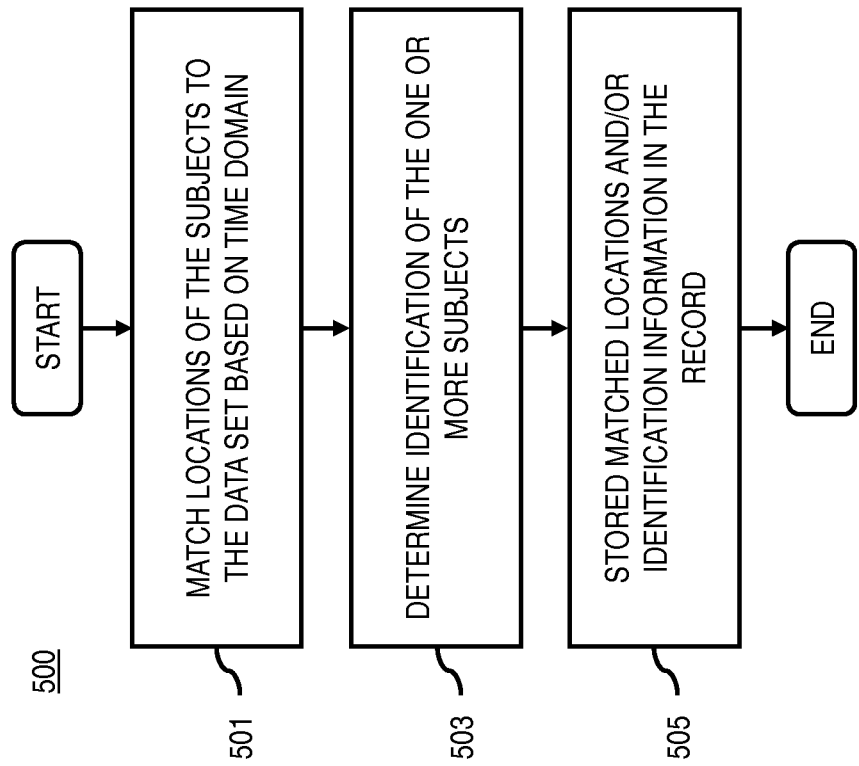
FIG. 5 is a flowchart of a process for determining identification information and matched locations for vital sign information matching, according to one example embodiment.

FIG. 5 is a flowchart of a process for determining identification information and matched locations for vital sign information matching, according to one example embodiment. In one embodiment, the vital matching platform 101 performs the process 500 and is implemented in, for instance, a chip set including a processor and a memory as shown in FIG. 11. In addition or alternatively, the vital matching client 103 can perform all or a portion of the process 500. In one embodiment, the process 500 provides optional steps that can be performed as part of the process 400 of FIG. 4.

In step 501, if the sensors are configured with the option to monitor location information, the vital matching platform 101 matches the one or more locations of the one or more objects 111 to the concurrently recorded data set based on the time domain. Because the sensors 109 in this embodiment can measure both vital signs and locations of tracked objects 111, the vital matching platform 101 can record either or both the vital signs and locations into one record. Alternatively, separate records of the vital signs and locations (still matched according to a time domain) can be maintained.

In step 503, the vital matching platform 101 determines identification information for the one or more objects based on the sensor information, the one or more vital signs, profile information associated with the one or more objects, or a combination thereof. As previously discussed, object identification information can vary in specificity from anonymous to exact name, identifier, etc. depending on, e.g., service and/or privacy requirements. If more specific identification of objects 111 is desired, the vital matching platform 101 can perform additional optional steps to determine identification information for tracked objects.

In one embodiment, the vital matching platform 101 processes and/or facilitates a processing of other sensor information collected from one or more other sensors to determine the identification. In one embodiment, the other sensor information includes image data, and wherein the image data is processed using an image recognition process to determine the identification information. As discussed previously, the other sensor information can be collected from other sensors in the monitored area 107 such as the recording device 121, the UE 113, or any other device capable of recording or generating a data set 119 concurrently (in time) with the collection of the vital sign and location measurements.

In one embodiment, the vital matching platform 101 matches the one or more vital signs to previously identified vital sign data to determine the identification information. For example, if more specific identification is requested, the vital matching platform 101 can search previously identified vital sign data for similarities or matches to the vital signs of the tracked objects 111. If there is a similarity or match, the vital matching platform 101 can assign the known identity to the matched object 111. In one embodiment, vital sign matching can be performed using pattern matching or any other method for assessing whether one set of vital signs matches another set of vital signs.

In step 505, the vital matching platform 101 stores the one or more locations matched according to the time domain and/or the identification information in the at least one record.

Figure 6:
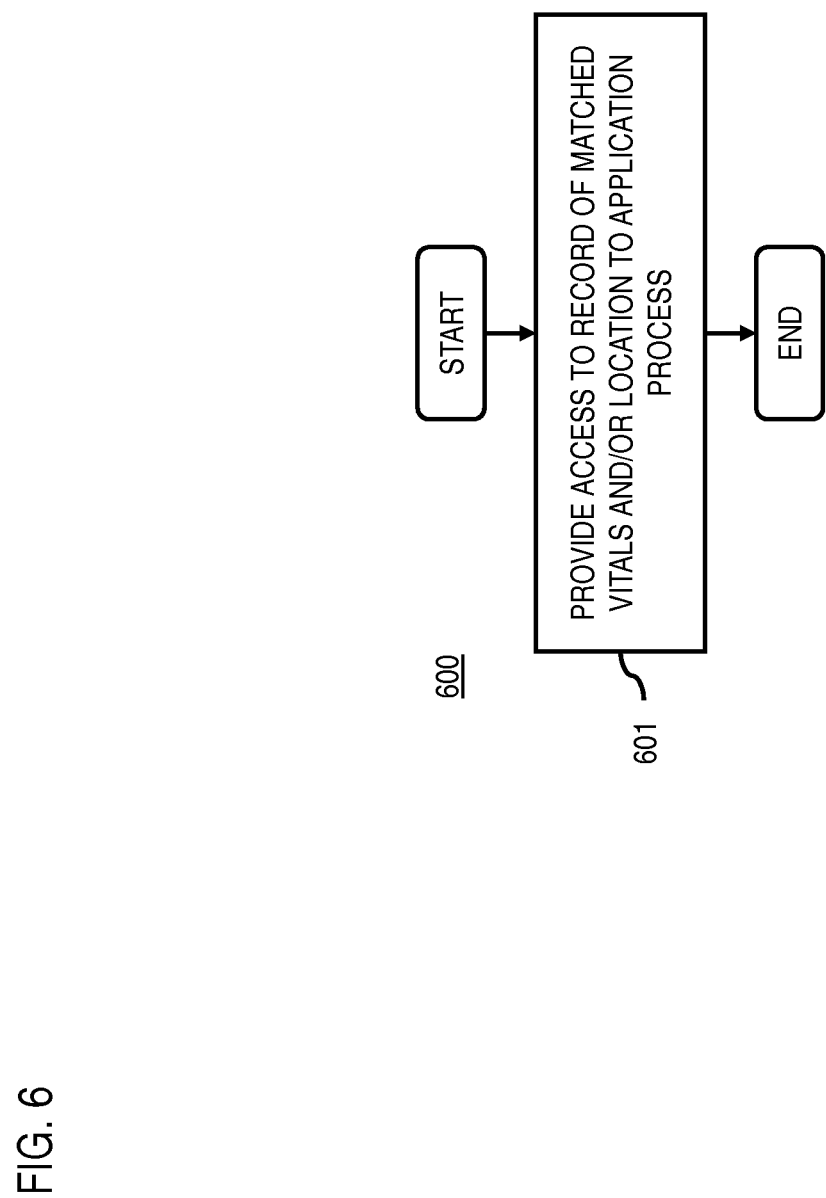
FIG. 6 is a flowchart of a process for providing access to a matched vital sign information record, according to one example embodiment.

FIG. 6 is a flowchart of a process for providing access to a matched vital sign information record, according to one example embodiment. In one embodiment, the vital matching platform 101 performs the process 600 and is implemented in, for instance, a chip set including a processor and a memory as shown in FIG. 11. In addition or alternatively, the vital matching client 103 can perform all or a portion of the process 600.

In step 601, the vital matching platform 101 provides an access to the at least one record to at least one application process. In one embodiment, the application process reads the data from the record and performs one or more actions based on the at least one record.

In one embodiment, the application process initiates the one or more actions based on the one or more vital signs in the at least one record. By way of example, actions can be related to any number of uses cases based on the service or application being provided. In one example use case, the application process determines at least one behavior associated with the one or more objects based on the at least record, and wherein the application process initiates the one or more actions based on the at least one behavior.

In another use case, the application process detects at least one emergency condition associated with the one or more objects, the one or more locations of the one or more objects, one or movements of the one or more objects as indicated by the one or more locations, or a combination thereof; and wherein the application process requests the at least one record based on the at least one emergency condition. The application process then determines the one or more actions based on the at least one emergency condition.

In yet another use case, the application process uses the at least one record to determine one or more reactions of the one or more objects to the concurrently recorded data set, and wherein the application process determines the one or more reactions based on the one or more vital signs, the one or more locations of the one or more objects, or a combination thereof.

Figure 7:
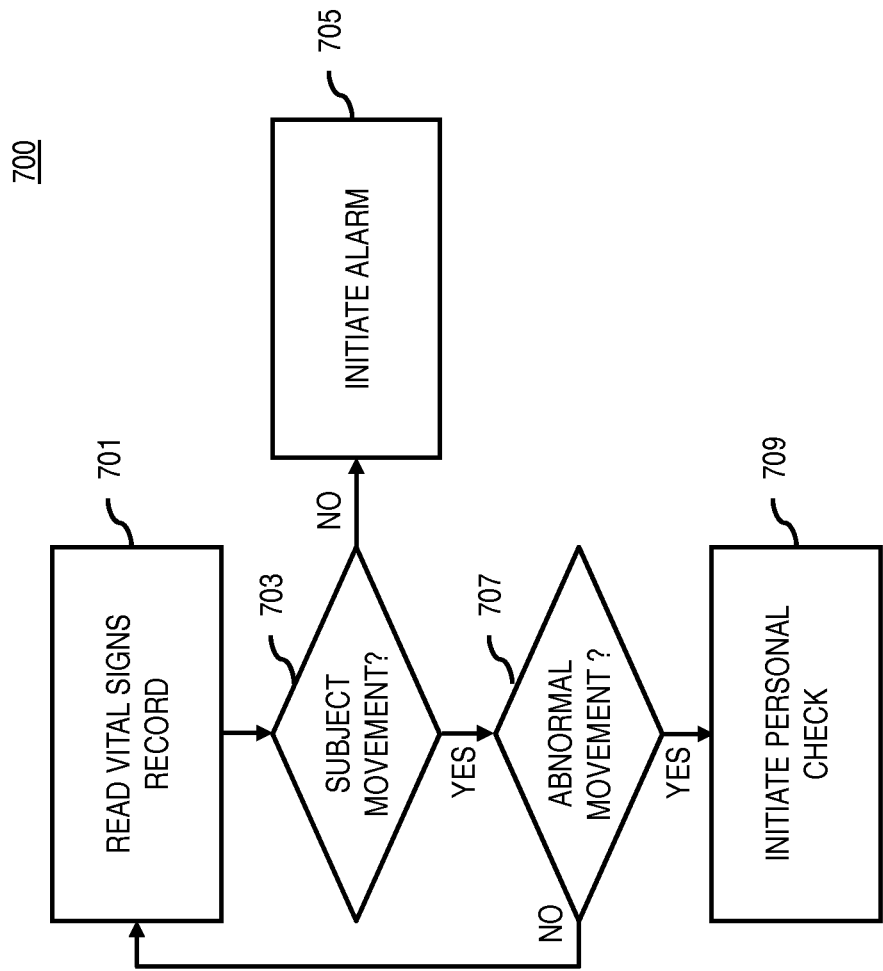
FIG. 7 is a diagram of a process for providing health monitoring using a matched vital sign information, according to one example embodiment.

FIG. 7 is a diagram of a process for providing health monitoring using a matched vital sign information, according to one example embodiment. In one embodiment, the an application process performs the process 700 and is implemented in, for instance, a chip set including a processor and a memory as shown in FIG. 11 using information generated by the vital matching platform 101.

The example of FIG. 7 illustrates an example use case for tracking and monitoring people who may be vulnerable to or suffer from health conditions (e.g., elderly or sick people in supported living conditions). In this example, a service 123 associated with the application process can be based on installing a measurement and tracking device (e.g., a radio reflection measurement technology sensor 109 as previously described above) in rooms of a supported or assisted living facility. The measurement data (e.g., vital sign and location information) can be sent to a cloud storage of the service 123 where the data can be further processed so that a monitored person's vital signs can be matched to an actual identity and/or to translate a relative location (as measured by the sensors 109) into an absolute location within the monitored facility (e.g., by calculating the absolute location from the relative location to a known location of the corresponding sensor 109). In one embodiment, a health monitoring application (e.g., used by a health authority or some other interested party) can then utilize the data to track conditions of the people (e.g., elderly or sick people) and send alarm notifications if abnormal behavior or other behavior indicating a problem is detected.

Process 700 is an example process for this type of application as shown in FIG. 7. In step 701, the application process read the vital sign records for objects 111 (e.g., persons) tracked using the vital sign monitoring processes described herein. Multiple people can be tracked at the same in same data record (e.g., using radio reflection measurement technology), and the application process can query for a specific individual or evaluate all individuals recorded in the vital sign records. For example, the query can ask for a person by name, ID number, or some other identifier.

The application process then extracts the locations of a person of interest from the vital sign records, and determines movements of the person based on the changes (if any in location over time). In step 703, for instance, the application person can determine whether there is any movement of the subject as determined from the vital signs record. If there is no movement for more than a predetermined period of time, the application can initiate an alarm notification to responsible authorities (at step 705).

If there is movement detected, the application process can then determine whether the movement is abnormal (at 707). For example, the application process can evaluate the movement patterns determined from the vital sign records against known patterns of abnormal movement or criteria indicating abnormal movement. The criteria may include, e.g., slow or fast movements, movements that change direction erratically, unstable movements, etc. In one embodiment, the application process can evaluate the concurrent vital sign information when determining whether there is abnormal movement (e.g., slow movement coupled with a high heart rate or respiration rate). If the determined movement is classified as abnormal then then still can initiate or send a request to a responsible authority to check a personal or wellness check of the person (step 709). If the movement is not abnormal, the application returns to step 701 and continues to monitor.

Figure 8:
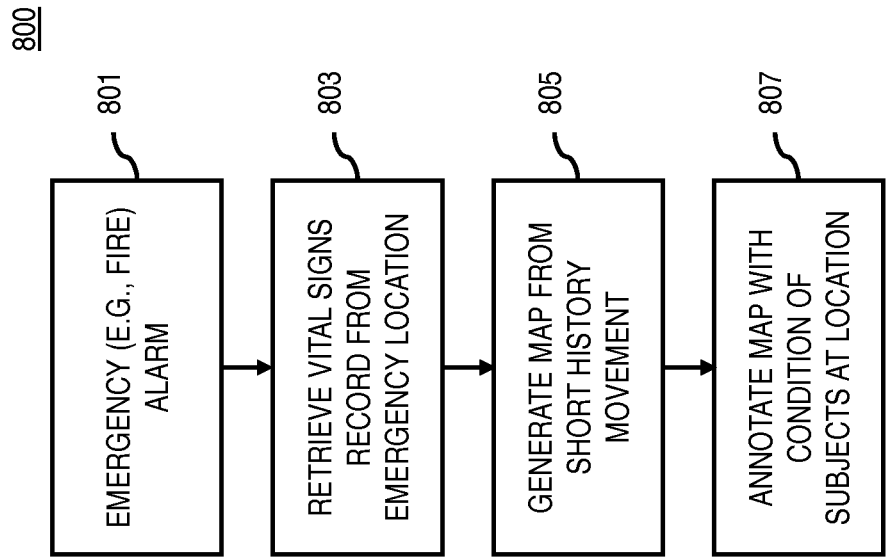
FIG. 8 is a diagram of a process for using matched vital sign information for providing emergency services, according to one example embodiment.

FIG. 8 is a diagram of a process for using matched vital sign information for providing emergency services, according to one example embodiment. In one embodiment, the an application process performs the process 700 and is implemented in, for instance, a chip set including a processor and a memory as shown in FIG. 11 using information generated by the vital matching platform 101.

The example of FIG. 8 illustrates an example use for tracking and monitoring people who may be present at a location with an active emergency (e.g., a fire alarm, a police emergency, etc.). In this example, vital sign and location tracking sensors 109 can be installed at a monitored location. An emergency service 123 can then access the vital sign/location information of people at the monitored location during an emergency. For example, the application process (e.g., a rescue authority application provided by the emergency service 123) can receive basic information of the locations of people, historical status of movement (e.g., over a short period of time), and health status so that rescue personnel can local vulnerable people and triage the rescue effort (e.g., define a rescue order for the people detected), which may be guided by vital signs.

In step 801, the service 123 detects that an emergency alarm (e.g., fire alarm) has been activated at a location. The service 123 then retrieves vital signs records from the emergency location. In one embodiment, the records include vital sign and location information for all persons detected at the location (at step 803). In another embodiment, only information associated with a subset or selected persons are retrieved.

The application process then processes the information to extract vital sign information and location information over a period of time (e.g., within the past 15 mins, or some other time period) to generate a map indicating a short history of movement for the tracked person (e.g., to aid in locating and rescuing the person) (at step 805).

In one embodiment, the application process can annotate the map with the health condition of the subjects or persons at the location (at step 807). For example, the health condition can be indicated by the vital sign information monitored from each tracked subject. In this way, rescue personnel can prioritize which subjects to rescue first based on which subjects appear to be in more health distress. An example map is illustrated in FIG. 9 discussed below.

Figure 9:
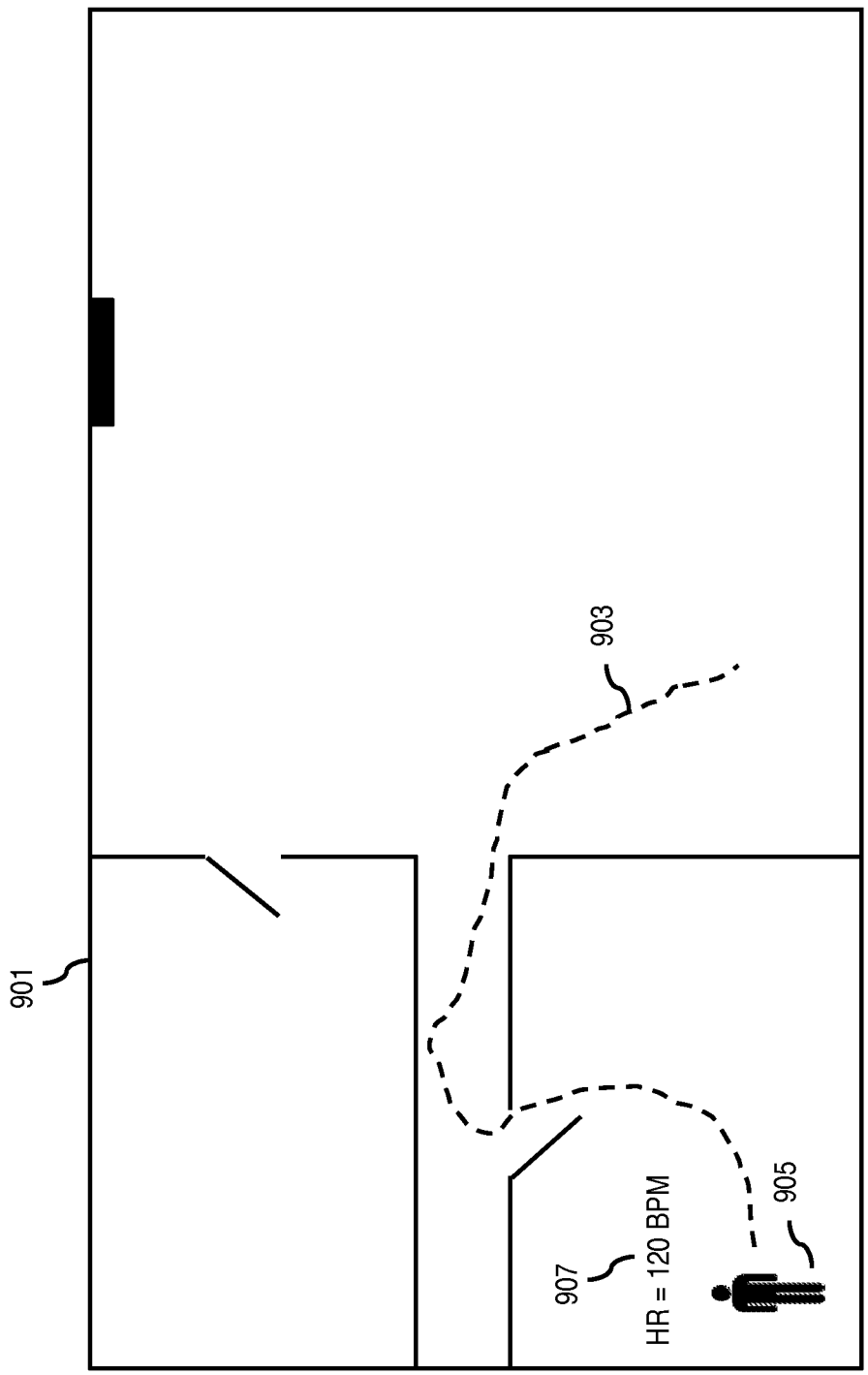
FIG. 9 is a diagram of an example user interface for providing emergency services using matched vital sign information, according to one embodiment.

FIG. 9 is a diagram of an example user interface for providing emergency services using matched vital sign information, according to one embodiment. In one embodiment, the emergency service 123 of FIG. 8 produces a map 901 of the building and overlays the tracked movement 903 of a tracked person 905. The map 901 can also be annotated with the vital signs 907 of the tracked person 905 to provide status information to emergency personnel. In one embodiment, the service 123 can present the map 901 in a user interface of devices (e.g., UEs 113) associated with emergency personnel.

The processes described herein for providing matching vital sign information to a concurrently recorded data set according to a time domain may be advantageously implemented via software, hardware (e.g., general processor, Digital Signal Processing (DSP) chip, an Application Specific Integrated Circuit (ASIC), Field Programmable Gate Arrays (FPGAs), etc.), firmware or a combination thereof. Such exemplary hardware for performing the described functions is detailed below.

Figure 10:
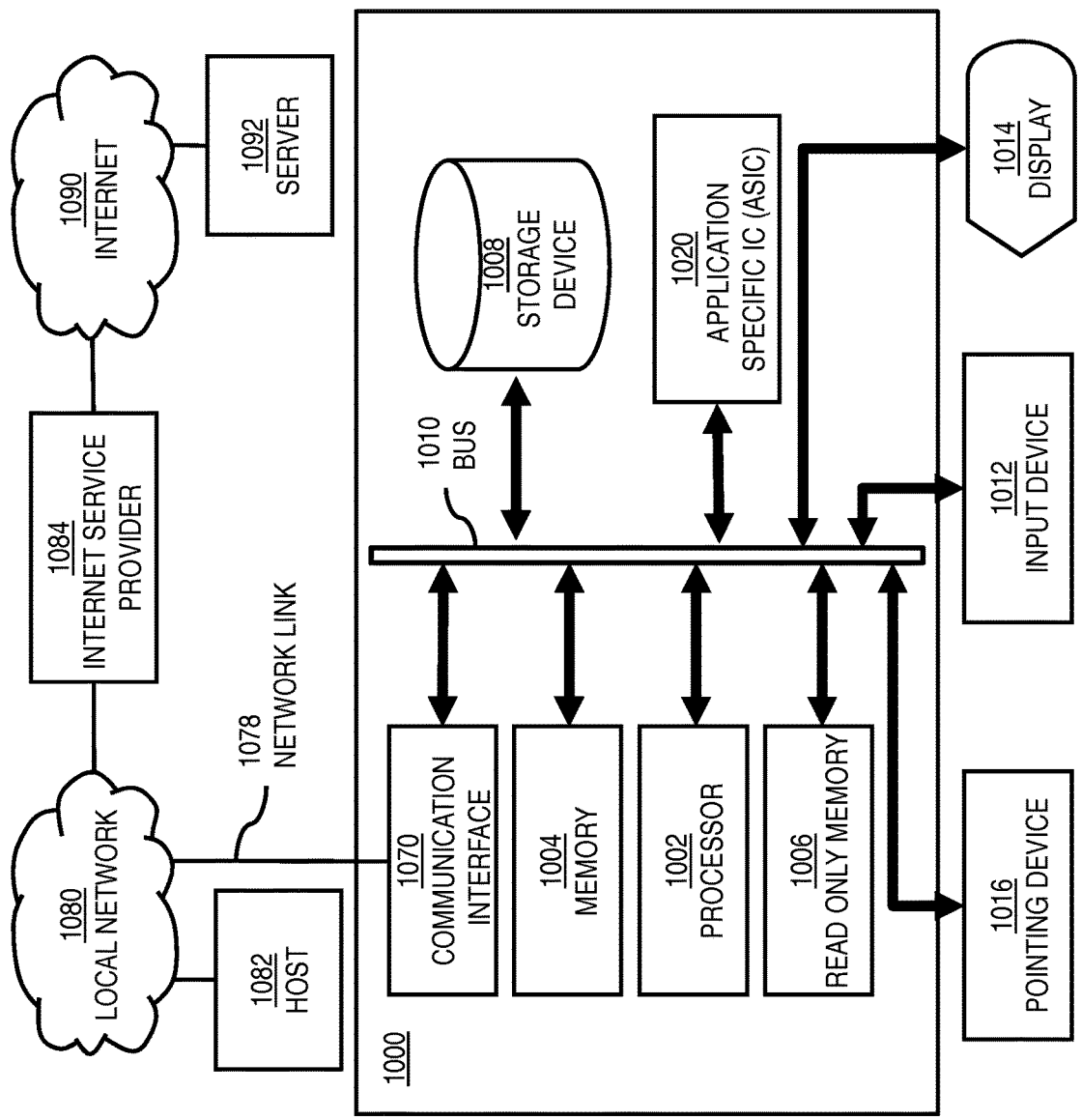
FIG. 10 is a diagram of hardware that can be used to implement an embodiment of the invention.

FIG. 10 illustrates a computer system 1000 upon which an embodiment of the invention may be implemented. Computer system 1000 is programmed (e.g., via computer program code or instructions) to match vital sign information to a concurrently recorded data set according to a time domain as described herein and includes a communication mechanism such as a bus 1010 for passing information between other internal and external components of the computer system 1000. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range.

A bus 1010 includes one or more parallel conductors of information so that information is transferred quickly among devices coupled to the bus 1010. One or more processors 1002 for processing information are coupled with the bus 1010.

A processor 1002 performs a set of operations on information as specified by computer program code related to matching vital sign information to a concurrently recorded data set according to a time domain. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 1010 and placing information on the bus 1010. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 1002, such as a sequence of operation codes, constitute processor instructions, also called computer system instructions or, simply, computer instructions. Processors may be implemented as mechanical, electrical, magnetic, optical, chemical or quantum components, among others, alone or in combination.

Computer system 1000 also includes a memory 1004 coupled to bus 1010. The memory 1004, such as a random access memory (RAM) or other dynamic storage device, stores information including processor instructions for matching vital sign information to a concurrently recorded data set according to a time domain. Dynamic memory allows information stored therein to be changed by the computer system 1000. RAM allows a unit of information stored at a location called a memory address to be stored and retrieved independently of information at neighboring addresses. The memory 1004 is also used by the processor 1002 to store temporary values during execution of processor instructions. The computer system 1000 also includes a read only memory (ROM) 1006 or other static storage device coupled to the bus 1010 for storing static information, including instructions, that is not changed by the computer system 1000. Some memory is composed of volatile storage that loses the information stored thereon when power is lost. Also coupled to bus 1010 is a non-volatile (persistent) storage device 1008, such as a magnetic disk, optical disk or flash card, for storing information, including instructions, that persists even when the computer system 1000 is turned off or otherwise loses power.

Information, including instructions for matching vital sign information to a concurrently recorded data set according to a time domain, is provided to the bus 1010 for use by the processor from an external input device 1012, such as a keyboard containing alphanumeric keys operated by a human user, or a sensor. A sensor detects conditions in its vicinity and transforms those detections into physical expression compatible with the measurable phenomenon used to represent information in computer system 1000. Other external devices coupled to bus 1010, used primarily for interacting with humans, include a display device 1014, such as a cathode ray tube (CRT) or a liquid crystal display (LCD), or plasma screen or printer for presenting text or images, and a pointing device 1016, such as a mouse or a trackball or cursor direction keys, or motion sensor, for controlling a position of a small cursor image presented on the display 1014 and issuing commands associated with graphical elements presented on the display 1014. In some embodiments, for example, in embodiments in which the computer system 1000 performs all functions automatically without human input, one or more of external input device 1012, display device 1014 and pointing device 1016 is omitted.

In the illustrated embodiment, special purpose hardware, such as an application specific integrated circuit (ASIC) 1020, is coupled to bus 1010. The special purpose hardware is configured to perform operations not performed by processor 1002 quickly enough for special purposes. Examples of application specific ICs include graphics accelerator cards for generating images for display 1014, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1000 also includes one or more instances of a communications interface 1070 coupled to bus 1010. Communication interface 1070 provides a one-way or two-way communication coupling to a variety of external devices that operate with their own processors, such as printers, scanners and external disks. In general the coupling is with a network link 1078 that is connected to a local network 1080 to which a variety of external devices with their own processors are connected. For example, communication interface 1070 may be a parallel port or a serial port or a universal serial bus (USB) port on a personal computer. In some embodiments, communications interface 1070 is an integrated services digital network (ISDN) card or a digital subscriber line (DSL) card or a telephone modem that provides an information communication connection to a corresponding type of telephone line. In some embodiments, a communication interface 1070 is a cable modem that converts signals on bus 1010 into signals for a communication connection over a coaxial cable or into optical signals for a communication connection over a fiber optic cable. As another example, communications interface 1070 may be a local area network (LAN) card to provide a data communication connection to a compatible LAN, such as Ethernet. Wireless links may also be implemented. For wireless links, the communications interface 1070 sends or receives or both sends and receives electrical, acoustic or electromagnetic signals, including infrared and optical signals, that carry information streams, such as digital data. For example, in wireless handheld devices, such as mobile telephones like cell phones, the communications interface 1070 includes a radio band electromagnetic transmitter and receiver called a radio transceiver. In certain embodiments, the communications interface 1070 enables connection to the communication network 107 for matching vital sign information to a concurrently recorded data set according to a time domain.

The term computer-readable medium is used herein to refer to any medium that participates in providing information to processor 1002, including instructions for execution. Such a medium may take many forms, including, but not limited to, non-volatile media, volatile media and transmission media. Non-volatile media include, for example, optical or magnetic disks, such as storage device 1008. Volatile media include, for example, dynamic memory 1004. Transmission media include, for example, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, any other memory chip or cartridge, a carrier wave, or any other medium from which a computer can read.

FIG. 11 illustrates a chip set 1100 upon which an embodiment of the invention may be implemented. Chip set 1100 is programmed to match vital sign information to a concurrently recorded data set according to a time domain as described herein and includes, for instance, the processor and memory components described with respect to FIG. 10 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip.

In one embodiment, the chip set 1100 includes a communication mechanism such as a bus 1101 for passing information among the components of the chip set 1100. A processor 1103 has connectivity to the bus 1101 to execute instructions and process information stored in, for example, a memory 1105. The processor 1103 may include one or more processing cores with each core configured to perform independently. A multi-core processor enables multiprocessing within a single physical package. Examples of a multi-core processor include two, four, eight, or greater numbers of processing cores. Alternatively or in addition, the processor 1103 may include one or more microprocessors configured in tandem via the bus 1101 to enable independent execution of instructions, pipelining, and multithreading. The processor 1103 may also be accompanied with one or more specialized components to perform certain processing functions and tasks such as one or more digital signal processors (DSP) 1107, or one or more application-specific integrated circuits (ASIC) 1109. A DSP 1107 typically is configured to process real-world signals (e.g., sound) in real time independently of the processor 1103. Similarly, an ASIC 1109 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1103 and accompanying components have connectivity to the memory 1105 via the bus 1101. The memory 1105 includes both dynamic memory (e.g., RAM, magnetic disk, writable optical disk, etc.) and static memory (e.g., ROM, CD-ROM, etc.) for storing executable instructions that when executed perform the inventive steps described herein to match vital sign information to a concurrently recorded data set according to a time domain. The memory 1105 also stores the data associated with or generated by the execution of the inventive steps.

FIG. 12 is a diagram of exemplary components of a mobile station (e.g., handset) capable of operating in the system of FIG. 1, according to one embodiment. Generally, a radio receiver is often defined in terms of front-end and back-end characteristics. The front-end of the receiver encompasses all of the Radio Frequency (RF) circuitry whereas the back-end encompasses all of the base-band processing circuitry. Pertinent internal components of the telephone include a Main Control Unit (MCU) 1203, a Digital Signal Processor (DSP) 1205, and a receiver/transmitter unit including a microphone gain control unit and a speaker gain control unit. A main display unit 1207 provides a display to the user in support of various applications and mobile station functions that offer automatic contact matching. An audio function circuitry 1209 includes a microphone 1211 and microphone amplifier that amplifies the speech signal output from the microphone 1211. The amplified speech signal output from the microphone 1211 is fed to a coder/decoder (CODEC) 1213.

A radio section 1215 amplifies power and converts frequency in order to communicate with a base station, which is included in a mobile communication system, via antenna 1217. The power amplifier (PA) 1219 and the transmitter/modulation circuitry are operationally responsive to the MCU 1203, with an output from the PA 1219 coupled to the duplexer 1221 or circulator or antenna switch, as known in the art. The PA 1219 also couples to a battery interface and power control unit 1220.

In use, a user of mobile station 1201 speaks into the microphone 1211 and his or her voice along with any detected background noise is converted into an analog voltage. The analog voltage is then converted into a digital signal through the Analog to Digital Converter (ADC) 1223. The control unit 1203 routes the digital signal into the DSP 1205 for processing therein, such as channel encoding, encrypting, and interleaving. In one embodiment, the processed voice signals are encoded, by units not separately shown, using a cellular transmission protocol such as global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wireless fidelity (WiFi), satellite, and the like.

The encoded signals are then routed to an equalizer 1225 for compensation of any frequency-dependent impairments that occur during transmission though the air such as phase and amplitude distortion. After equalizing the bit stream, the modulator 1227 combines the signal with a RF signal generated in the RF interface 1229. The modulator 1227 generates a sine wave by way of frequency or phase modulation. In order to prepare the signal for transmission, an up-converter 1231 combines the sine wave output from the modulator 1227 with another sine wave generated by a synthesizer 1233 to achieve the desired frequency of transmission. The signal is then sent through a PA 1219 to increase the signal to an appropriate power level. In practical systems, the PA 1219 acts as a variable gain amplifier whose gain is controlled by the DSP 1205 from information received from a network base station. The signal is then filtered within the duplexer 1221 and optionally sent to an antenna coupler 1235 to match impedances to provide maximum power transfer. Finally, the signal is transmitted via antenna 1217 to a local base station. An automatic gain control (AGC) can be supplied to control the gain of the final stages of the receiver. The signals may be forwarded from there to a remote telephone which may be another cellular telephone, other mobile phone or a land-line connected to a Public Switched Telephone Network (PSTN), or other telephony networks.

Voice signals transmitted to the mobile station 1201 are received via antenna 1217 and immediately amplified by a low noise amplifier (LNA) 1237. A down-converter 1239 lowers the carrier frequency while the demodulator 1241 strips away the RF leaving only a digital bit stream. The signal then goes through the equalizer 1225 and is processed by the DSP 1205. A Digital to Analog Converter (DAC) 1243 converts the signal and the resulting output is transmitted to the user through the speaker 1245, all under control of a Main Control Unit (MCU) 1203—which can be implemented as a Central Processing Unit (CPU) (not shown).

The MCU 1203 receives various signals including input signals from the keyboard 1247. The keyboard 1247 and/or the MCU 1203 in combination with other user input components (e.g., the microphone 1211) comprise a user interface circuitry for managing user input. The MCU 1203 runs a user interface software to facilitate user control of at least some functions of the mobile station 1201 to match vital sign information to a concurrently recorded data set according to a time domain. The MCU 1203 also delivers a display command and a switch command to the display 1207 and to the speech output switching controller, respectively. Further, the MCU 1203 exchanges information with the DSP 1205 and can access an optionally incorporated SIM card 1249 and a memory 1251. In addition, the MCU 1203 executes various control functions required of the station. The DSP 1205 may, depending upon the implementation, perform any of a variety of conventional digital processing functions on the voice signals. Additionally, DSP 1205 determines the background noise level of the local environment from the signals detected by microphone 1211 and sets the gain of microphone 1211 to a level selected to compensate for the natural tendency of the user of the mobile station 1201.

The CODEC 1213 is associated with the ADC 1223 and DAC 1243. The memory 1251 stores various data including call incoming tone data and is capable of storing other data including music data received via, e.g., the global Internet. The software module could reside in RAM memory, flash memory, registers, or any other form of writable storage medium known in the art. The memory device 1251 may be, but not limited to, a single memory, CD, DVD, ROM, RAM, EEPROM, optical storage, or any other non-volatile storage medium capable of storing digital data.

An optionally incorporated SIM card 1249 carries, for instance, important information, such as the cellular phone number, the carrier supplying service, subscription details, and security information. The SIM card 1249 serves primarily to identify the mobile station 1201 on a radio network. The card 1249 also contains a memory for storing a personal telephone number registry, text messages, and user specific mobile station settings.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

The invention claimed is:

1. A method comprising:
   determining, by a network device of the communication network, sensor information collected from one or more sensors configured to monitor one or more vital signs of one or more objects within a monitored area;
   processing the sensor information to detect the one or more objects and to track the one or more vital signs of the one or more objects over a time domain time;
   matching the one or more vital signs of the one or more objects to a concurrently recorded data set that was recorded during processing the one or more vital signs of the one or more objects over the time domain using a determined time correlation in the time domain between measurements of the one or more vital signs and the concurrently recorded data, wherein the determined time correlation is based at least on information of a relative one or more locations of the one or more objects to the one or more sensors; and
   storing as metadata at least one record of the one or more vital signs that are matched to the concurrently recorded data set according to the determined time correlation in the time domain, and wherein the concurrently recorded data set includes a media file, and wherein the storing comprises:
   making available at the network device the at least one record of the one or more vital signs matched to the concurrently recorded data set according to the determined time correlation in the time domain in the media file as metadata associated with the media file.

2. A method of claim 1, wherein the one or more sensors are further configured to monitor one or more locations of the one or more objects, and wherein the sensor information includes the one or more locations.

3. A method according to claim 1, wherein the one or more sensors employ a radio signal reflection measurement technology to remotely determine the one or more vital signs, the relative one or more locations of the one or more objects to the one or more sensors, or a combination thereof.

4. A method according to claim 2, further comprising:
   based on the processing over the time domain, matching the one or more locations of the one or more objects to the concurrently recorded data set; and
   storing the one or more locations matched according to the time domain in the at least one record.

5. A method according to claim 1, further comprising:
   determining identification information for the one or more objects based on the sensor information, the one or more vital signs, profile information associated with the one or more objects, or a combination thereof; and
   storing the identification data in the at least one record.

6. An apparatus comprising:
   at least one processor; and
   at least one memory including computer program code for one or more programs, the at least one memory and the computer program code configured to, with the at least one processor, cause the apparatus to perform at least the following,
   determine sensor information collected from one or more sensors configured to monitor one or more vital signs of one or more objects within a monitored area;
   process the sensor information to detect the one or more objects and to track the one or more vital signs of the one or more objects over a time domain;
   match the one or more vital signs of the one or more objects to a concurrently recorded data set that was recorded during processing the one or more vital signs of the one or more objects over the time domain using a determined time correlation in the time domain between measurements of the one or more vital signs and the concurrently recorded data, wherein the determined time correlation is based at least on information of a relative one or more locations of the one or more objects to the one or more sensors; and
   store as metadata at least one record of the one or more vital signs that are matched to the concurrently recorded data set according to the determined time correlation in the time domain, wherein the concurrently recorded data set includes a media file, and wherein the apparatus is further caused to:
   make available at the apparatus the at least one record of the one or more vital signs matched to the concurrently recorded data set according to the determined time correlation in the time domain in the media file as metadata associated with the media file.

7. An apparatus of claim 6, wherein the one or more sensors are further configured to monitor one or more locations of the one or more objects, and wherein the sensor information includes the one or more locations.

8. An apparatus according to claim 6, wherein the one or more sensors employ a radio signal reflection measurement technology to remotely determine the one or more vital signs, the relative one or more locations of the one or more objects to the one or more sensors, or a combination thereof.

9. An apparatus according to claim 7, wherein the apparatus is further caused to:
match the one or more locations of the one or more objects to the concurrently recorded data set based on the time domain; and
store the one or more locations matched according to the time domain in the at least one record.

10. An apparatus according to claim 6, wherein the apparatus is further caused to:
determine identification information for the one or more objects based on the sensor information, the one or more vital signs, profile information associated with the one or more objects, or a combination thereof; and
store the identification data in the at least one record.

11. An apparatus of claim 10, wherein the apparatus is further caused to:
process other sensor information collected from one or more other sensors to determine the identification information.

12. An apparatus of claim 11, wherein the other sensor information include image data, and wherein the image data is processed using an image recognition process to determine the identification information.

13. An apparatus according to claim 10, wherein the apparatus is further caused to:
match the one or more vital signs to previously identified vital sign data to determine the identification information.

14. An apparatus according to claim 6, wherein the apparatus is further caused to:
provide an access to the at least one record to at least one application process,
wherein the application process reads the data from the record and performs one or more actions based on the at least one record.

15. An apparatus of claim 14, wherein the application process initiates the one or more actions based on the one or more vital signs in the at least one record.

16. An apparatus according to claim 14, wherein the application process determines at least one behavior associated with the one or more objects based on the at least record, and wherein the application process initiates the one or more actions based on the at least one behavior.

17. An apparatus according to claim 14, wherein the application process detects at least one emergency condition associated with the one or more objects, the one or more locations of the one or more objects, one or movements of the one or more objects as indicated by the one or more locations, or a combination thereof; and wherein the application process requests the at least one record based on the at least one emergency condition.

18. An apparatus of claim 17, wherein the application process determines the one or more actions based on the at least one emergency condition.

19. An apparatus according to claim 14, wherein the application process uses the at least one record to determine one or more reactions of the one or more objects to the concurrently recorded data set, and wherein the application process determines the one or more reactions based on the one or more vital signs, the one or more locations of the one or more objects, or a combination thereof.

* * * * *